United States Patent [19]

Schacht et al.

[11] Patent Number: 5,602,101

[45] Date of Patent: Feb. 11, 1997

[54] ANTITHROMBOTIC AGENTS

[75] Inventors: Aaron L. Schacht, Indianapolis; Robert T. Shuman, Greenwood; Gerald F. Smith, Indianapolis; James H. Wikel, Greenwood; Michael R. Wiley, Indianapolis, all of Ind.

[73] Assignee: Eli Lilly and Company, Indianapolis, Ind.

[21] Appl. No.: 318,600

[22] Filed: Oct. 5, 1994

Related U.S. Application Data

[63] Continuation-in-part of Ser. No. 206,500, Mar. 4, 1994, abandoned.

[51] Int. Cl.$^6$ .............................. C07K 5/00; C07K 7/00; C07K 17/00; A61K 38/00

[52] U.S. Cl. .................. 514/18; 514/19; 530/331; 548/953; 548/535; 544/55; 544/58.5; 544/60; 544/96; 544/111; 544/124; 544/242; 546/208

[58] Field of Search .................................. 548/953, 535; 544/55, 58.5, 60, 96, 111, 224, 242; 546/208; 530/331; 514/18, 19

[56] References Cited

U.S. PATENT DOCUMENTS

| | | | |
|---|---|---|---|
| 4,316,889 | 2/1982 | Bajusz et al. | 424/177 |
| 4,346,078 | 8/1982 | Bajusz et al. | 424/177 |
| 4,399,065 | 8/1983 | Bajusz et al. | |
| 4,478,745 | 10/1984 | Bajusz et al. | |
| 4,703,036 | 10/1987 | Bajusz et al. | 514/18 |
| 5,053,392 | 10/1991 | Klein et al. | 514/18 |
| 5,153,176 | 10/1992 | Abe et al. | 514/18 |
| 5,202,416 | 4/1993 | Steuber et al. | 530/322 |
| 5,204,323 | 4/1993 | Findlay et al. | 514/2 |
| 5,250,660 | 10/1993 | Shuman et al. | 530/344 |
| 5,252,566 | 10/1993 | Shuman | 514/210 |
| 5,380,713 | 1/1995 | Balasubramanian et al. | 514/18 |
| 5,416,093 | 5/1995 | Shuman | 514/307 |
| 5,430,023 | 7/1995 | Gesellchen et al. | 514/18 |
| 5,436,229 | 7/1995 | Ruterbories et al. | 514/18 |
| 5,439,888 | 8/1995 | Shuman et al. | 514/18 |
| 5,484,772 | 1/1996 | Sall et al. | 514/18 |
| 5,488,037 | 1/1996 | Sall et al. | 514/19 |

FOREIGN PATENT DOCUMENTS

| | | |
|---|---|---|
| 16380/95 | 4/1995 | Australia . |
| 21801/95 | 6/1995 | Australia . |
| 293881 | 12/1988 | European Pat. Off. . |
| 410411 | 1/1991 | European Pat. Off. . |
| 479489 | 4/1992 | European Pat. Off. . |
| 526877 | 8/1992 | European Pat. Off. . |
| 503203 | 9/1992 | European Pat. Off. . |
| 504064 | 9/1992 | European Pat. Off. . |
| 529568 | 3/1993 | European Pat. Off. . |
| 530167 | 3/1993 | European Pat. Off. . |
| 542525 | 5/1993 | European Pat. Off. . |
| 648780 | 8/1994 | European Pat. Off. . |
| WO93/08211 | 4/1993 | WIPO . |
| WO93/11152 | 6/1993 | WIPO . |
| WO93/15756 | 8/1993 | WIPO . |
| WO95/09858 | 4/1994 | WIPO . |
| WO94/29335 | 12/1994 | WIPO . |
| WO94/29336 | 12/1994 | WIPO . |
| WO95/09634 | 4/1995 | WIPO . |
| WO95/09859 | 4/1995 | WIPO . |

OTHER PUBLICATIONS

Jackson et al, Arteriosclerosis and Thrombosis vol. 11 p. 1586a, abstract.

Wilson et al, Arteriosclerosis and Thrombosis vol. 11 p. 1586a, abstract.

Bajusz et al Int. J. Peptide Protein Res. vol. 12 p. 217 (1978).

Bajusz et al, J. Med. Chem. vol. 33 p. 1729 (1990).

Shuman, Peptide, Proc. 12th Am. Peptide Symposium Jun. 16–21, 1991 p. 801.

Bajusz, S., et al., *J. Med. Chem.*, 1990, 33, 1729–1735.

Fareed, J., et al., *Annals N.Y. Academy of Sciences*, 1981, 765–784.

Shuman, et al., Proceedings of the Twelfth American Peptide Symposium, Jun. 16–21, 1991, pp. 799–802. Abst.

Wilson, et al., American Heart Association, Nov. 11–14, 1991, Anaheim Convention Center, Anaheim, CA, Abstract.

Bajusz, et al., *Int. J. Peptide Res.*, 12, 1978, 217–221.

Gesellchen, et al., Tenth American Peptide Symposium, May 23–28, 1987, St. Louis, MO Abst.

Claeson, et al., Proceedings of the Twelfth American Peptide symposium, Jun. 16–14 21, 1991, Cambridge, MA, pp. 824–825.

Smith, G. F., Shuman, R. T. Gesellchen, P. D., Craft, T. J., Gifford, P., Kurz, K. D., Jackson, C. V., Sandusky, G. E., and P. D. Williams, A New Family of Thrombin Inhibitors with Improved Specificity and Therapeutic Index. (Submitted to the American Heart Association, Oct., 1991, Circulation Oct., 1991, vol. 84, II–579, 1991), Abstract.

Jackson, V., Wilson, H., Frank, J., Crowe, V., Craft, T., and G. Smith. The Thrombin Inhibitor, Methyl–D–Phe–P-ro–Arginal—An Effective Adjunct to Coronary Artery Thrombolysis in the Anesthetized Dog. FASEB J. 5(4)A520 (1991) #365.

Crowe, V., Frank, J., Wilson, H., Coffman, B., Smith, G., and V. Jackson. Anticoagulant and Antithrombotic Efficacy of the Novel Thrombin Inhibitor Methyl–D–Phg–Pro–Arginal in a Canine Model of Coronary Thrombosis. FASEB J. 5(4)AS520 (1991) #864.

Wilson, H., Frank J., Crowe, V., Coffman, B., Smith, G., Shuman, R., and V. Jackson. Anticoagulant and Antithrombotic Efficacy of the Novel Thrombin Inhibitor, Methyl–D–Phy–Pro–Arginal, in a Canine Model of Coronary Thrombosis (Arteriosclerosis and Thrombosis, 11(5), Oct., 1991) p. 1586a.

(List continued on next page.)

*Primary Examiner*—Toni R. Scheiner
*Assistant Examiner*—Sheela J. Huff
*Attorney, Agent, or Firm*—Thomas E. Jackson; David E. Boone; John C. Demeter

[57] ABSTRACT

This invention relates to L-Arginine aldehyde derivatives, pharmaceutical formulations containing those compounds and methods of their use as thrombin inhibitors, coagulation inhibitors and thromboembolic disorder agents.

90 Claims, No Drawings

OTHER PUBLICATIONS

Jackson, V., Wilson, H., Frank, J., Crowe, V., Coffman, B., Shuman, R., and G. Smith. The Novel Thrombin Inhibitor Methyl–D–Phg–Pro–Arginal: An Effective Conjunctive Agent to Coronary Artery Thrombolysis in the Anesthetized Dog. (Arteriosclerosis and Thrombosis, 11(5), Oct., 1991) p. 1586a.

Shuman, R. T., Rothenberger, R. B., Campbell, C. S., Smith, G. F., Jackson, C. V., Kurz, K. D., and P. D. Gesellchen. Prevention of Reocclusion by a Thrombin Inhibitor. (American Peptide Symposium, Jun., 1991, pp. 799–800).

Shuman, R. T., Rothenberger, R. B., Campbell, C. S., Smith, G. F., Jackson, C. V., Kurz, K. D., and P. D. Gesellchen. A Series of Highly Active Serine Proteinase Inhibitors. (American Peptide Symposium, Jun. 1991, pp. 801–802).

Jackson, C. V., Frank, J. D., Crowe, V. G., Craft, T. J., and G. F. Smith. Assessment of the Anticoagulant and Antithrombotic Efficacy of the Thrombin Inhibitor, BOC–Phe–Pro–Arginal, in a Canine Model of Coronary Thrombosis. *Arteriosclerosis*, 10 922A (1990)–Abst.

Jackson, C. V., Frank, J. D., Crowe, V. G., Craft, T. J., and G. F. Smith. The Thrombin Inhibitor, BOC–D–Phe–Pro–Arginal. An Effective Adjunct to Coronary Artery Thrombolysis in the Anesthetized Dog. *Arteriosclerosis*, 10 923a (1990).

Shackelford, K. A., Tanzer, R. L., Shuman, R., Gesellchen, P. D., Grindey, G. B., Sundboom, J. L., Smith, G. F., and R. L. Merriman. Inhibition of Spontaneous Metastasis by Boc–D–Phe–Pro–Arginal. American Association for Cancer Research, San Francisco, 1989. *Proc. Am. Assn. Cancer Res.*, 30 86, 1989.

Neubauer, B. L., Clemens, J. A., Gesellchen, P. D., Hirsch, K. S., Hoover, D. M., Merriman, R. L., and G. F. Smith. Endocrine Characterization and Sensitivity of the PAIII Prostatic Adenocarcinoma in Male Lobund–Wistar (LW) Rats to Anti–Fibrin Agents. American Association for Cancer Research. New Orleans, May 1988, *Proc. Am. Assn. Cancer Res.*, 29 240 (1988).

Neubauer, B. L., Best, K. L., Gesellchen, P. D., Goode, R. L., Merriman, R. L., Tanzer, L. R., Shaar, C. J., Shuman, R., Sundboom, Pro–Arginal on the Metastasis of the PAIII Prostatic Adenocarcinoma in Male Lobund Wistar (LW) Rats. American Urological Association. Boston, May 1988, *J. Urol.*, 139 175A (1988).

Gesellchen, P. D., Smith, G. F., et al., Anticoagulant, Antithrombotic, and Antimetastatic Effects of a Serine Proteinase Inhibitor. 10th American Peptide Symposium, Washington University, St. Louis, MO (1987), Abstract.

Smith, G. F., Sundboom, J. L., Best, K., Gesellchen, P. D., Merriman, R. L., Shuman, R., and Neubauer, B. L. Heparin, Boc–D0–Phe–Pro–Arginal, and Warfarin (Fibrin Antagonists) Inhibit Metastasis in an In Vivo Model. American Chemical Society National Meeting. Abstract BIOL 70 Biochemistry (1987).

K. D. Kurz, T. Smith, R. A. Moore and B. W. Main. Comparison of Thrombin Inhibitors in Rat Models of Thrombosis and Thrombolysis. FASEB Journal, vol. 5 (No. 4), 1991, Abstract #886.

Tomori, et al., *Chromatographia*, vol. 19, 437–442 (1984).

Dayhoff, *Atlas of Protein Sequence and Structure*, 5, pp. 85–89 (1972).

Shuman, et al., *J. Med. Chem.*, 36(3), 314–319 (1993).

Jackson, et al., *J. Cardiovasc. Pharmacol.*, 21(4), 587–594 (1993).

Cheng, et al., *Tetrahedron Lett.*, 32 (49), 7333–7336 (1991).

Bagdy, et al., *Thrombosis and Haemostasis*, 68(2), 125–129 (1992).

*Thrombosis and Haemostasis*, 65, 1289, Nos. 2150–2151 and 2152 (1991).

Bagdy, et al., *Thrombosis and Haemostasis*, 67(3), 325–330 (1992).

Bagdy, et al., *Thrombosis and Haemostasis*, 67(3), 357–365 (1992).

Balasubramanian, et al., *J. Med. Chem.*, 36, 300–303 (1993).

Shuman, et al., Oral Activity of Tripeptide Aldehyde Thrombin Inhibitors, Thirteenth American Peptide Symposium, Jun. 20–25, 1993, Abstract.

Kurz et al., Antithrombotic Efficacy in the Rat After Intravenous and Oral Administration of a Direct Inhibitor of Thrombin FASEB, Mar. 28–Apr. 1, 1993.

Iwanowicz, et al., *Bioorg. Med. Chem. Lett.*, 2(12), 1607–1612 (1992).

Barabas, et al., *Blood Coagul. Fibrin.*, 4, 243–248 (1993).

Jackson, et al., Conjunctive Therapy with the Thrombin Inhibitor, LY 294468, and Aspirin Produced Enhanced Antireocclusive Activity When Used in a Canine Model of Streptokinase–Induced Coronary Thrombolysis, *The Pharmacologist*, 35(3), 207 (1993), Abstract #407.

Pozagay, et al., Study of the Specificity of Thrombin with Tripeptidyl–p–Nitroanilide Substrates, *Eur. J. Biochem.*, 115, 491–495 (1981).

Jackson, et al., *The Journal of Pharmacology and Experimental Therapy*, 261(2), 546–552 (1992).

Stueber, et al., Proc. of the 13th American Peptide Symposium, Jun. 20–25, 1993.

Stürzebecher, et al., XIVth Congress of the International Society on Thrombosis and Hemostasis, Jul. 4–9, 1993.

Simoons et al., *Circulation*, 90, I–231, Abstr. 1241 (1994).

ANTITHROMBOTIC AGENTS

This is a continuation-in-part of application Ser. No. 08/206,500, filed Mar. 4, 1994 and now abandoned.

BACKGROUND OF THE INVENTION

This invention relates to thrombin inhibitors which are useful anticoagulants in mammals. In particular it relates to L-Arginine aldehyde derivatives having high anticoagulant activity, and antithrombotic activity.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation is currently achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and safety, heparin levels must be monitored with coagulation assays (particularly the activated partial thromboplastin time (APTT) assay). Coumarins impede the generation of thrombin by blocking the posttranslational gammacarboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729–1735 (1990) demonstrate potent direct inhibition of thrombin. Many investigators have synthesized analogs in an effort to develop pharmaceutical agents, for example Shuman et al. *J. Med. Chem.*, 96, 314–319 (1993), as well as European patent applications, publication numbers 479489, 542525 and 530167.

Although the heparins and coumarins are effective anticoagulants, and no drug has yet emerged from the known tripeptide aldehydes, and despite the continuing promise for this class of compounds, there exists a need for anticoagulants that act selectively on thrombin, and independent of antithrombin III, exert inhibitory action shortly after administration, and do not interfere with lysis of blood clots, as required to maintain hemostasis.

The present invention is directed to the discovery that the compounds of the present invention, as defined below, are potent thrombin inhibitors.

Accordingly, it is a primary object of the present invention to provide novel L-Arginine aldehyde derivatives that are potent thrombin inhibitors useful as anticoagulants.

Other objects features and advantages will be apparent to those skilled in the art from the following description and claims.

SUMMARY OF THE INVENTION

The present invention provides thrombin inhibiting compounds having the formula

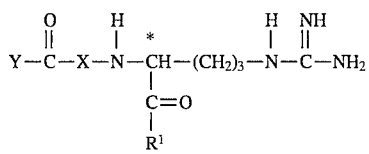

where $R^1$ is hydrogen;

X is prolinyl or azetidinyl-2-carbonyl;

Y is a group

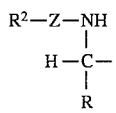

where R is benzyl, phenyl, cyclopentyl, cyclohexyl, cyclopentyl-$CH_2$— or cyclohexyl-$CH_2$—;

Z is

—$S(O)_n$— or a bond;

$R_2$ is $C_1$–$C_6$ alkyl, $C_1$–$C_2$ perfluoroalkyl, —$(CH_2)_g$—COOH, $C_1$–$C_6$ alkoxy, ($C_1$–$C_4$ alkoxy)$C_1$–$C_4$ alkyl, cyclopentyl, cyclohexyl, ($C_5$–$C_6$ cycloalkyl)$CH_2$—, amino, mono ($C_1$–$C_4$) alkylamino, di ($C_1$–$C_4$) alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

g is 1, 2 or 3;

n is 1 or 2; and pharmaceutically acceptable salts and solvates thereof;

provided that when R is benzyl, phenyl, cyclopentyl or cyclohexyl and z is

or a bond, $R^2$ is other than $C_1$–$C_6$ alkyl, $C_{1-C2}$ perfluoroalkyl or $C_1$–$C_6$ alkoxy.

A particular subgroup of compounds of formula I of the invention consists of those compounds of formula I where $R^1$ is hydrogen;

X is prolinyl or azetidinyl-2-carbonyl;

Y is a group

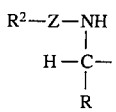

where R is benzyl, phenyl, cyclopentyl, cyclohexyl, cyclopentyl-CH$_2$— or cyclohexyl-CH$_2$—;

Z is

—S(O)$_n$— or a bond;

R$^2$ is C$_1$–C$_6$ alkyl, C$_1$–C$_2$ perfluoroalkyl, C$_1$–C$_6$ alkoxy, (C$_1$–C$_4$ alkoxy)C$_{1-C4}$ alkyl, cyclopentyl, cyclohexyl, (C$_5$–C$_6$ cycloalkyl)CH$_2$—, amino, mono (C$_1$–C$_4$)alkylamino, di(C$_{1-C4}$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

n is 1 or 2; and pharmaceutically acceptable salts and solvates thereof;

provided that when R is benzyl, phenyl, cyclopentyl or cyclohexyl and Z is

or a bond, R$^2$ is other than C$_1$–C$_6$ alkyl, C$_1$–C$_2$ perfluoroalkyl or C$_1$–C$_6$ alkoxy.

In addition to the compounds of formula I, the present invention provides pharmaceutical formulations comprising a compound of formula I in association with a pharmaceutically acceptable carrier, diluent or excipient.

The present invention also provides a method of inhibiting coagulation in mammals comprising administering to a mammal in need of treatment, a coagulation inhibiting dose of a compound of formula I.

The present invention further provides a method of inhibiting thrombin comprising administering to a mammal in need of treatment, a thrombin inhibiting dose of a compound of formula I.

Further, the present invention provides a method of treating thromboembolic disorders comprising administering to a mammal requiring treatment, an effective dose of a compound of formula I.

DETAILED DESCRIPTION OF THE INVENTION

This invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent means a straight or branched chain alkyl radical having the stated number of carbon atoms such as methyl, ethyl, n-propyl, isopropyl, n-butyl, t-butyl, isobutyl and sec-butyl.

The term "alkoxy" means a straight or branched chain alkyl radical having the stated number of carbon atoms bonded to the parent moiety by an oxygen atom. The term "halo" means chloro, fluoro, bromo or iodo.

The term "di(C$_1$–C$_4$ alkyl)amino" means a group —N(C$_{1-C4}$ alkyl)$_2$ where each alkyl group, independently, has the stated number of carbon atoms.

The term "perfluoroalkyl" means a straight or branched chain alkyl radical having the stated number of carbon atoms with all available valences substituted with fluoro atoms such as trifluoromethyl and pentafluoro ethyl.

The term "5 or 6 membered heterocyclic ring" means any 5 or 6 membered ring that will afford a stable structure containing one nitrogen atom; one nitrogen and one sulfur atom; one nitrogen and one oxygen atom; or two nitrogen atoms. Heterocyclics include pyrrolyl, pyrazolyl, oxazolyl, isoxazolyl, thiazolyl, isothiazolyl, oxadiazolyl, pyranyl, pyridinyl, pyrimidinyl, pyrazinyl and oxazinyl.

The term "9 or 10 membered fused bicyclic heterocyclic ring" means any bicyclic group in which any of the above 5 or 6 membered rings is fused to a benzene ring or a cyclohexane ring that will afford a stable structure. These heterocyclics include indolyl, benzoxazolyl, benziosoxazolyl, benzopyrazolyl, quinolinyl, isoquinolinyl, benzimidazolyl and benzothiazolyl.

The above heterocycles may exist in tautomeric forms. All such forms are included within the scope of the invention.

The groups

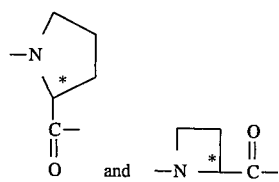

are referred to as prolinyl and azetidine-2-carbonyl, respectively, and are respectively abbreviated Pro and Azt.

The carbonyl functionality of X is attached to the amino group drawn in formula I All of the above heterocycles, phenyl and the aromatic ring of benzyl are unsubstituted or substituted with one or two substituents that will afford a stable structure independently selected from halo, hydroxy, C$_1$–C$_4$ alkyl, C$_1$–C$_4$ alkoxy, carboxy, amino (—NH$_2$), mono(C$_1$–C$_4$ alkyl)amino, di(C$_1$–C$_4$ alkyl)amino, —N(C$_1$–C$_4$ alkyl)$_2$, mercapto, C$_1$–C$_4$alkylthio (—S (O)$_p$C$_1$–C$_4$ alkyl); —NHS (O)$_p$(C$_1$–C$_4$ alkyl), —NHC (O)C$_1$–C$_4$ alkyl, —S (O)$_p$NH$_2$, —S(O)$_p$NH(C$_1$–C$_4$ alkyl), and —S(O)$_p$N(C$_1$–C$_4$ alkyl)$_2$, where p is 1 or 2.

The asterisks in formula I and substituent X denote a chiral center that is (L).

In addition, diastereomers exist at the Y substituent and, depending on substitutions on said Y substituent, further diastereomers may exist. The compounds of the present invention include mixtures of two or more diastereomers as well as each individual isomer.

Preferred compounds of the present invention include those compounds of formula I where $R^1$ is hydrogen;

$R^2$ is $C_1$–$C_6$ alkyl, amino, mono ($C_1$–$C_4$ alkyl) amino, di ($C_1$–$C_4$ alkyl)amino, or a 9 or 10 membered unsubstituted or monosubstituted fused bicyclic heterocyclic ring; and where X, R and Z are as defined above for formula I and pharmaceutically acceptable salts and solvates thereof; provided that when R is benzyl, phenyl, cyclopentyl or cyclohexyl and Z is

or a bond, $R^2$ is other than $C_1$–$C_6$ alkyl.

A first group of particularly preferred compounds of the present invention are those compounds of formula I where $R^1$ is hydrogen;

X is prolinyl or azetidinyl-2-carbonyl;

R is benzyl or cyclohexyl-$CH_2$—;

Z is

$R^2$ is a 9 or 10 membered unsubstituted or monosubstituted fused bicyclic heterocyclic ring containing one nitrogen atom and where the substituent is selected from $C_1$–$C_4$ alkyl, amino, mono($C_1$–$C_4$ alkyl)amino, di($C_1$–$C_4$ alkyl)amino, and —$NHSO_2$($C_1$–$C_4$ alkyl);

and pharmaceutically acceptable salts and solvates thereof.

A second group of particularly preferred compounds of the present invention are those compounds of formula I where $R^1$ is hydrogen;

X is prolinyl or azetidinyl-2-carbonyl;

Z is —$SO_2$—;

$R^2$ is $C_1$–$C_6$ alkyl, amino, mono($C_1$–$C_4$ alkyl)amino or di ($C_1$–$C_4$ alkyl) amino;

and R is as defined above for formula I;

and pharmaceutically acceptable salts and solvates thereof.

A third group of particularly preferred compounds of the present invention consists of those compounds of formula I where $R^1$ is hydrogen;

X is prolinyl or azetidinyl-2-carbonyl;

z is a bond;

$R^2$ is —$(CH_2)_g$—COOH;

g is 1, 2 or 3 (and, more particularly, g is 1); and

R is as defined above for formula I;

and pharmaceutically acceptable salts and solvates thereof. These compounds have unexpectedly improved oral bioavailability and increased inhibition of factor Xa compared to the corresponding compounds lacking the carboxy group.

As mentioned above, the invention includes pharmaceutically acceptable salts of the compounds defined by the above formula I. A particular compound of this invention can possess one or more sufficiently basic functional groups, and accordingly react with any of a number of nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

As stated above, the present invention includes solvates of the compounds of formula I and the pharmaceutically acceptable salts thereof. A particular compound of the present invention or a pharmaceutically acceptable salt thereof may form solvates with water or common organic solvents. Such solvates are included within the scope of compounds of the present invention.

The compounds of formula I are prepared by known methods of peptide coupling. According to one such method the acid PY-COOH, where Y has the same meanings as defined for formula I, and P is an amino protecting group, is coupled with a carboxy protected proline (or azetidine-2-carboxy ester) to form the dipeptide. For a compound of formula I in which Y includes a carboxy group, P also denotes a carboxy protecting group, which may be in addition to an amino protecting group. The carboxy protecting ester group of the proline moiety is then removed (deblocked or deesterified) and the free acid form of dipeptide is coupled with the lactam form of arginine. The above reaction sequence is illustrated by the following Scheme 1:

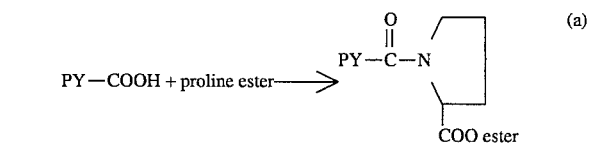

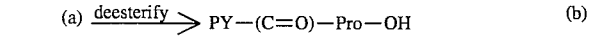

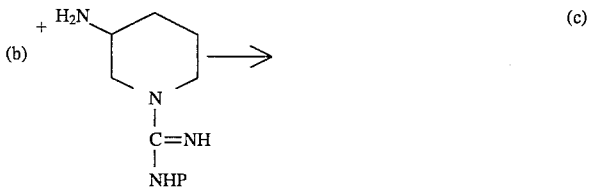

wherein P represents an amino protecting group.

The coupled Arg(P) lactam product (c) is reacted with a hydride reducing agent, preferably lithium aluminum hydride or lithium tritert-butoxyaluminohydride, in an inert solvent or mixture of solvents to reduce the lactam ring and provide the tripeptide in the arginine aldehyde form represented by the formula

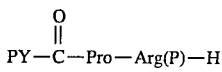

wherein (P) represents amino protecting groups.

The protecting groups are removed by procedures known to those skilled in the art such as hydrogenation over a metal catalyst.

The lactam form of arginine is obtained by intramolecular coupling of amino protected arginine [Arg-OH]. For example, Boc-Arg(Cbz)OH represented by the formula

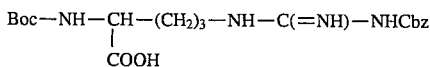

where Boc is t-butyloxycarbonyl and Cbz is benzyloxycarbonyl is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of further or another tertiary amine base, such as triethylamine or diisopropylethylamine, effects the internal acylation to provide the lactam form of the di-amino protected arginine as shown below

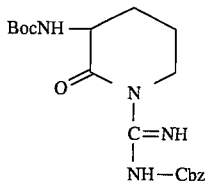

Prior to use in the coupling with the PY(C=O)-Pro-OH as shown in the above scheme, the Boc or other amine protecting group is selectively removed with trifluoroacetic acid or HCl to provide the requisite free amino group.

The coupling of an PYCOOH compound with a proline ester, when Y is as defined above for formula I, is carried out by first protecting the amino group of the amino acid. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl) prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichlorethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group, and the like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the benzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction an ester protecting group for proline is employed which is removable by conditions under which the amino protecting group remains intact. The amino protecting group of the acylating acid PYCOOH thus remains in place for protection of the amino group during the subsequent coupling with the arginine lactam compound to form c.

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$–$C_3$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2'4,4'-tetramethoxybenzhydryl, t-butyl, t-amyl, trityl, 4-methoxytrityl, 4,4'-dimethoxytrityl, 4,4', 4"-trimethoxytrityl, 2-phenylprop-2-yl, trimethylsilyl, t-butyldimethylsilyl, phenacyl, 2,2,2-trichloroethyl, 2-(trimethylsilyl)ethyl, 2-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below). Preferred carboxy protecting groups are $C_1$–$C_3$ alkyl and benzyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Synthesis", John Wiley and Sons, New York, N.Y., 1981, Chapter 5.

The compounds of formula I where X is azetidinyl (or prolinyl) are prepared in an analogous manner by known methods of peptide coupling. According to one such method, the cyclic lactam form of arginine (e) is prepared and coupled with an amino protected azetidine-2-carboxylic acid (d) as shown below to afford the dipeptide (f)

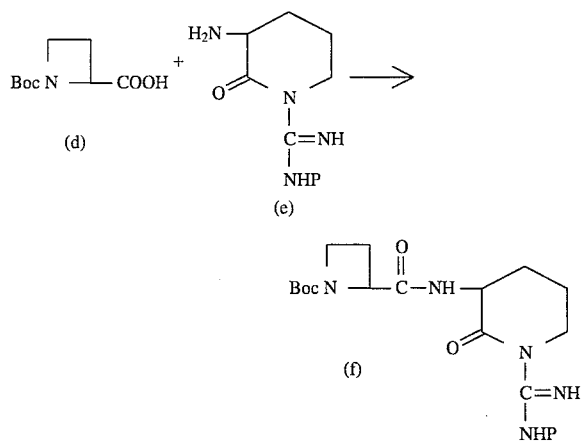

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and P. G. M. Wuts, Chapter 7, page 309–405 (1991), John Wiley & Sons, Inc., publishers. The Boc, or other suitable protecting group, is removed from the azetidine ring nitrogen which is then acylated with the desired amino acid acyl group to afford the tripeptide shown below.

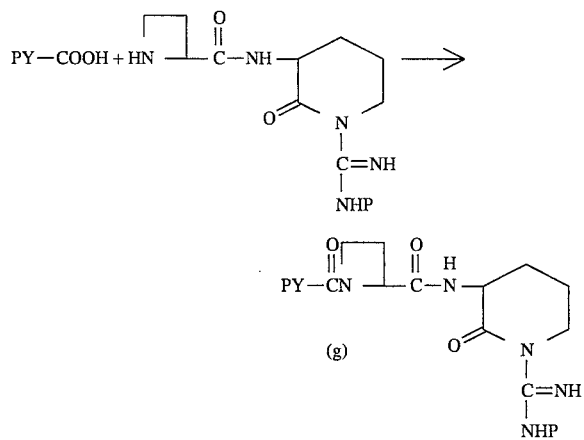

Although illustrated and described for those compounds of the present invention where X is azetidinyl-2-carbonyl, one skilled in the art will appreciate these procedures can also be used to afford those compounds of the present invention where X is prolinyl.

The coupled Arg(P) lactam product (g) is reduced with a hydride reducing agent, preferably lithium aluminum hydride or lithium tri-tert-butoxyaluminohydride in an inert solvent or mixture of solvents to reduce the lactam and provide the tripeptide in the arginine aldehyde form represented by the formula PY(C=O)-Azt-Arg(P)—H wherein P represents an amino protecting group. The protecting groups are removed by procedures known to those skilled in the art such as hydrogenation over a metal catalyst. The protecting groups may be removed from the Y-group and from the arginal group simultaneously or sequentially, depending upon the protecting groups utilized.

Alternatively, the compounds of the invention are prepared by coupling the PYCOOH acid with carboxy protected 2-azetidine-carboxylic acid. The carboxy is deprotected as the dipeptide which is then coupled with the amino protected arginine in the lactam form prepared as described above. The tripeptide is then reduced to provide the amino protected arginal tripeptide as described above.

The coupling of an PYCOOH compound is carried out by first protecting the amino group (and any other functionality which requires protection) of the amino acid. Conventional amino protecting groups commonly used for temporary protection or blocking of the amino group are employed. Examples of such protecting groups are described above.

The coupling reactions described above are carried out in the cold preferably at a temperature between about $-20°$ C. and about $15°$ C. The coupling reactions are carried out in an inert organic solvent such as dimethylformamide, dimethylacetamide, tetrahydrofuran, methylene chloride, chloroform, and like common solvents or a mixture of such solvents. Generally anhydrous conditions are used when, in the coupling reaction, an active ester of the acylating acid is used.

The compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalenesulfonic acid may be so used.

The preferred method for purifying the compounds of formula I, while at the same time preparing a desired stable salt form, is that described in U.S. Pat. No. 5,250,660, incorporated by reference herein. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile as the organic component. The pH of the acidic eluant is adjusted to between about pH 4 and about 6 with an anion exchange resin in the hydroxyl form e.g. Bio-Rad AG-1×8. After adjustment of the pH, the solution of tripeptide sulfate or hydrochloride salt is lyophilized to provide the pure salt in dry powder form. In an example of the process, crude N-ethylsulfonyl-D-phenylalanyl-L-Pro-L-Arg-H hydrochloride is dissolved in water and the solution is loaded on Vydac $C_{18}$ RPHPLC 5 cm×50 cm column. A gradient of 2–20% B (A=0.05% HCl; B=acetonitrile) over 10 hours is used. Multiple fractions are collected and those containing product as determined by analytical RPHPLC are pooled. The pH of the pooled fractions is adjusted to pH 4.0–4.5 with AG-1×8 resin in hydroxide form (Bio-Rad, 3300 Ragatta Blvd., Richmond, Calif. 94804). The solution is filtered and the filtrate is lyophilized to provide the pure D-,L-,L-, tripeptide aldehyde in the form of the hydrochloride salt.

The optically active isomers of the diastereomers of the Y substituent are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The following Examples are provided to further describe the invention and are not to be construed as limitations thereof.

The analytical HPLC methods used in the examples were as follows:

Method 1. Waters 600E using a Vydac $C_{18}$ reversed-phase column of 0.46 cm ×10 cm. The chromatogram was monitored on an LDC at 214 nM using a gradient of A=water containing 0.1% (v:v) TFA and B =acetonitrile containing 0.1% (v:v) TFA.

Method 2. Pharmacia FPLC using a Vydac $C_{18}$ reversed-phase column.measuring 0.46 cm ×10.0 cm. Monitoring was done on a Pharmacia UV-M at 214 nM using a gradient of either A=water containing 0.1% (v:v) TFA or B=acetonitrile containing 0.1% (v:v) TFA.

The abbreviations used in the examples have the following meanings.

Amino acids: Arg=arginine, Pro=proline, Phe=phenylalanine, Azt=azetidine-2-carboxylic acid Ac=acetyl
Boc=t-butyloxycarbonyl (t-butoxycarbonyl)
Bzl=benzyl
Cbz=benzyloxycarbonyl
Cha=cyclohexylalanyl
Chg=cyclohexylglycinyl
DCC=dicyclohexylcarbodiimide
DMF=dimethylformamide
DMSO=dimethylsulfoxide
EtOAc=ethyl acetate
Et₂O=diethyl ether
EtOH=ethanol
FAB-MS=fast atom bombardment mass spectrum
FD-MS=field desorption mass spectrum
HOBT=1-hydroxybenzotriazole hydrate
HPLC=High Performance Liquid Chromatography
MOC=methoxycarbonyl
NMI=N-methylindolyl-2-carbonyl
Ph=phenyl
Phg=phenylglycinyl
IR=Infrared spectrum
LAH=Lithium aluminum hydride
NMR=Nuclear Magnetic Resonance
RPHPLC=Reversed Phase High Performance Liquid Chromatography
TFA=trifluoroacetic acid
THF=tetrahydrofuran
TLC=thin layer chromatography Unless otherwise stated, pH adjustments and work up are with aqueous acid or base solutions. RPHPLC is carried out using 0.1% aqueous (v:v) HCl (designated "A" in the Examples) and acetonitrile (designated "B" in the Examples). Mixtures of A and B are v:v. Where $^1$H-NMR is shown, the product afforded by the reaction was characterized by proton NMR to confirm the described compound was obtained.

EXAMPLE 1

Preparation of N-(1-methylindolyl-2-carbonyl)-D-phenylalanyl-L-prolinyl-L-arginine Aldehyde Hydrochloride

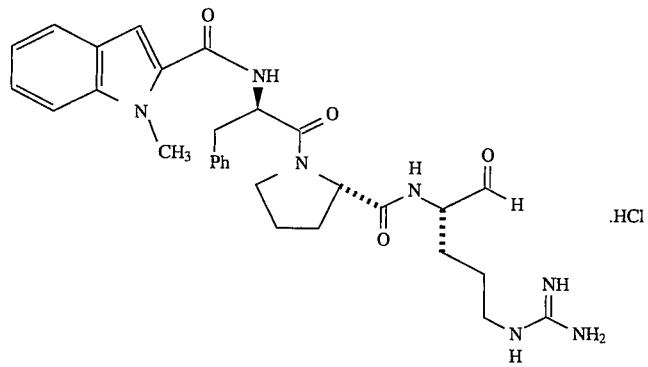

A) Boc-D-Phe-Pro-OBzl

To a solution of Boc-D-Phe-OH (89.1 g, 336 mmol), Pro-OBzl.HCl (81.2 g, 336 mmol), HOBT (50 g, 370 mmol) and N,N-diisopropylethylamine (176 mL, 1,008 mmol) at 0° C. in dichloromethane (600 mL) was added 1-(3-dimethylaminopropyl)-3-ethylcarbodiimide.HCl (71 g, 370 mmol). After stirring for 18 h, the mixture was diluted with diethyl ether (1 L) and washed three times with 1N citric acid (250 mL), once with water (250 mL), three times with sat'd aqueous NaHCO₃ (250 mL) and once with sat'd aqueous NaCl (250 mL). The organic phase was dried (Na₂SO₄), filtered, and concentrated in vacuo to yield 140 g (92.5%) of a pale yellow foam.

FD-MS, m/e 452 (M⁺)
$^1$H NMR

B) TFA. D-Phe-Pro-OBzl

To a stirring solution of Boc-D-Phe-Pro-OBzl (68 g, 150 mmol) in dichloromethane (50 mL) at 0° C., was added anisole (20 mL) followed by trifluoroacetic acid (400 mL). After stirring for 3 h, the solvents were evaporated in vacuo and the thick oily residue was dissolved in diethyl ether (1.5 L) and refrigerated (72 h). The white precipitate was filtered, washed diethyl ether (300 mL) and dried to yield 59.4 g (85%) of white powder.

1H NMR

C) NMI-D-Phe-Pro-OBzl

To a solution of N-methylindole-2-carboxylic acid (2.6 g, 14.9 mmol) in dry tetrahydrofuran (45 mL) was added pentafluorophenol (3 g, 16.5 mmol), followed by 1-(3-dimethylaminopropyl)-3-ethylcarbodiimide (3.2 g, 16.5 mmol). The mixture was allowed to stir at reflux for 3.5 h and then cooled to room temperature. Then, to this mixture was added a solution of TFA, D-Phe-Pro-OBzl (7 g, 14.9 mmol) and N,N-diisopropylethyl amine (4 g, 30 mmol) in tetrahydrofuran (25 mL). After stirring for an additional 2 h, the solvents were removed in vacuo and the residue was dissolved in ethyl acetate (500 mL), then washed three times with 0.1N aqueous $NaHSO_4$ (250 mL) and three times with 1N aqueous $K_2CO_3$ (250 mL). The organic phase was dried ($Na_2SO_4$), filtered, and concentrated in vacuo to give 6.5 g of amorphous solid (a mixture of the desired product, contaminated with pentafluorophenol).

1H NMR

FD-MS, m/e 509 ($M^+$)

D) NMI-D-Phe-Pro-OH

To a stirring solution of NMI-D-Phe-Pro-OBzl (8.8 g, 17.3 mmol) in p-dioxane (150 mL) was added a solution of $LiOH.H_2O$ (3.6 g, 86.3 mmol) in water (75 mL). After stirring for 4 h, the volume of the solution was reduced to about 50 mL in vacuo, and the solution was diluted with 1N NaOH (10 mL). The aqueous phase was washed three times with diethyl ether and then acidified to pH 2 with 5N HCl, and then extracted three times with ethyl acetate. The combined ethyl acetate extracts were washed with sat'd aqueous NaCl (200 mL), dried ($MgSO_4$), filtered and concentrated to give 5.4 g (75%) of white solid.

1H NMR

FD-MS, m/e 419 ($M^+$)

E) Boc-Arg(Cbz)-OH

Boc-Arg(HCl)-OH (82.1 g, 250 mmol) was dissolved in 5 N NaOH (240 mL) in a 3 necked flask. The reaction mixture was chilled to −5° C. and the pH was maintained at 13.2–13.5 using 5 N NaOH (250 mL) while adding benzyl chloroformate (143 mL, 1.0 mol) dropwise (55 min). The reaction mixture was stirred for an additional 1 hour at −5° C. and diluted with water (100 mL) and diethyl ether (500 mL). The aqueous layer was separated and extracted twice with diethyl ether (500 mL). The aqueous layer was then acidified to pH 3.0 with 3N $H_2SO_4$ (560 mL) and extracted with ethyl acetate (550 mL). The aqueous layer was separated and extracted once with ethyl acetate. The combined ethyl acetate layers were washed with water, dried ($MgSO)_4$) and concentrated in vacuo to give 66.1 g (65%) of a white solid:

$_1$H NMR

FD-MS 408 ($M^+$)

F) Boc-Arg(Cbz)-Lactam

Boc-Arg(Cbz)-OH (66.0 g, 0.162 mol) was dissolved in tetrahydrofuran (230 mL) and cooled to −10 °C. To this solution was added N-methylmorpholine (18.7 mL, 0.17 mol) followed by isobutyl chloroformate (22.5 mL, 0.17 mol). After stirring 5 minutes at −10° C., triethylamine (23.5 mL, 0.17 mol) was added. After an additional 1 hour at −10° C., the mixture was allowed to warm to room temperature and stirring continued for 1 h at room temperature. The reaction mixture was then poured into 1 L of ice-water and the resulting precipitate was filtered, washed with cold water, and dried in vacuo. The product was crystallized from ethyl acetate to give 38 g (60%) of a white solid. $^1$H NMR

FD-MS 391 ($MH^+$)

2HCl.Arg(Cbz)-Lactam

A solution of HCl(g) saturated ethyl acetate (7.2 L) was added dropwise over 30 minutes to a solution of Boc-Arg(Cbz)-Lactam (641 g, 1.64 mol) dissolved in dichloromethane (3 L) at −10° C. After 1 h at −10° C. the cold bath was removed and the solution was allowed to warm to room temperature over 3 h. Diethyl ether (12 L) was added and the resulting precipitate was filtered, washed with diethyl ether, and dried in vacuo to give 580 g (97%)

FD-MS 291 ($MH^+$)

H) NMI-D-Phe-Pro-Arg(Cbz)lactam

In flask 1, NMI-D-Phe-Pro-OH (5.3 g, 12.5 mmol) was dissolved in dimethylformamide (60 mL), cooled to −15° C. and N-methylmorpholine (1.3 g, 12.5 mmol) was added, followed by isobutyl chloroformate (1.7 g, 12.5 mmol). The reaction mixture was allowed to stir at −15°C for 10 min.

In flask 2, 2HCl.Arg(Cbz)-Lactam (4.5 g, 12.5 mmol) was dissolved in dimethylformamide (60 mL), cooled to 0° C., and N,N-diisopropylethylamine (3.2 g, 25 mmol) was added.

The contents of flask 2 were added to flask 1 in one portion and then the cold bath was left unattended and the reaction mixture was allowed to slowly warm to room temperature (24 h). Then saturated aqueous $NaHCO_3$ (100 mL) was added and the solvent was removed in vacuo. The residue was partitioned between ethyl acetate and water and the layers were separated. The organic layer was washed twice with 0.01N HCl, twice with saturated $NaHCO_3$, and once with brine. The organic layer was dried ($Na_2SO_4$), and the filtrate was concentrated in vacuo. The residue was chromatographed over silica gel, eluting with 95:5 ethyl acetate:acetonitrile and then the product containing fractions (as judged by TLC) were combined and concentrated to give 5 g (58%) of a light yellow foam.

$^1$H NMR

FD-MS, m/e 691 ($M^+$)

| Analysis Calculated for $C_{38}H_{41}N_7O_6$; | C 65.98, | H 5.97, | N 14.17; |
|---|---|---|---|
| Found; | C 66.28, | H 6.11, | N 13.94. |

I) NMI-D-Phe-Pro-Arg-H.HCl

To a stirring solution of NMI-D-Phe-Pro-Arg(Cbz)lactam (4.8 g, 6.9 mmol) in tetrahydrofuran (60 mL) at −78° C., was slowly added a solution of 1N lithium aluminum hydride (4.8 mL, 4.8 mmol) in tetrahydrofuran. After 30 min, the reaction mixture was poured into a stirring solution of cold 1N HCl (10 mL) and tetrahydrofuran (25 mL). The solution was then diluted with sat'd aqueous NaCl (50 mL) and extracted twice with ethyl acetate (100 mL). The combined ethyl acetate extracts were dried (MgSO4), filtered and concentrated to give 5.4 g of a yellow foam.

The foam was then dissolved in ethanol (75 mL) and water (25 mL) and this solution was added to a stirring solution of ethanol (75 mL), water (25 mL) and 1N HCl (10 mL). To this stirring solution was then added 5% Pd on carbon (2.4 g). $H_2$ was then bubbled through the solution for 1.5 h, and then the reaction was flushed with $N_2$ and filtered over a pad of Celite®. The ethanol was removed in vacuo at 35° C and then the residue was redissolved in water (25 mL). The pH of the aqueous solution was adjusted to 4.1 with Bio Rad ion exchange resin (basic form), filtered and lyophilized to give 3.4 g of a fluffy pale yellow solid. The product was then purified by RPHPLC (80/20 (A/B), 80 min; ramping up to 65/35 (A/B), 320 min; hold to 380 min, up to 0/100 (A/B) 440 min, hold to 500 min) to give 1.97 g (73%) of pure NMI-D-Phe-Pro-Arg-H.HCl hydrate.
$^1$H NMR
FAB-MS, m/e 560 (MH$^+$)

| Analysis Calculated for $C_{30}H_{37}N_7O_4 \cdot H_2O \cdot 1.2HCl$; | C 57.98, | H 6.52, | N 15.78; |
|---|---|---|---|
| Found; | C 58.25, | H 6.61, | N 15.33. |

EXAMPLE 2

Preparation of n-(quinolinyl-2-carbonyl)-D-phenylalanyl-L-prolinyl-L-arginine Aldehyde Hydrochloride

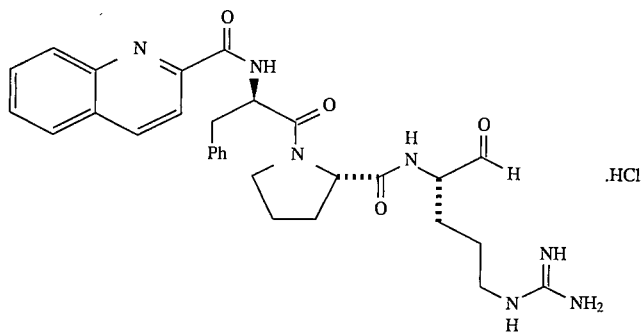

N-(quinoline-2-carbonyl)-D-Phe-Pro-H.HCl

By methods substantially equivalent to those described in Example 1-C, 1-D, 1-H and 1-I, 2.2 g of N-(quinoline-2-carbonyl)-D-Phe-Pro-H.HCl was prepared using quinoline-2-carboxylic acid in place of N-methylindole-2-carboxylic acid. N-(quinoline-2-carbonyl)-D-Phe-Pro-H.HCl was purified by RPHPLC (90/10 (A/B), 90 min; ramp to 70/30 (A/B), 390 min; ramp to 0/100 (A/B), 450 min; hold to 510 min).
$^1$H NMR
FAB-MS, m/e 558 (MH$^+$)

| Analysis Calc. for $C_{30}H_{35}N_7O_4 \cdot 1.1HCl \cdot 0.5H_2O$; | | | |
|---|---|---|---|
| Found; | C 59.39, | H 6.16, | N 16.16, | Cl 6.43; |
| | C 59.62, | H 5.98, | N 16.11, | Cl 6.38. |

EXAMPLE 3

Preparation of N-(nicotinoyl)-D-phenylalanyl-L-prolinyl-L-arginine Aldehyde Hydrochloride

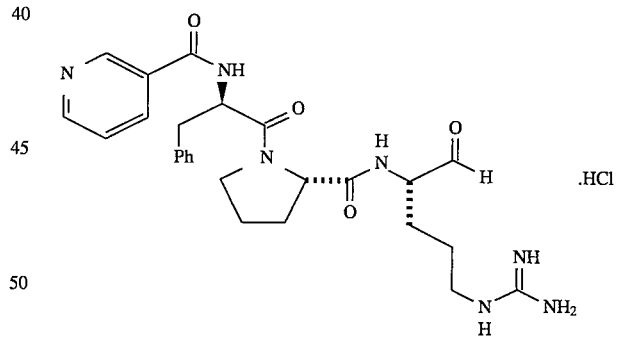

N-Nicotinoyl-D-Phe-Pro-Arg-H.HCl

By methods substantially equivalent to those described in Example 1-C, 1-D, 1-H and 1-I, 2.8 g of N-Nicotinoyl-D-Phe-Pro-Arg-H.HCl hydrate was prepared using nicotinic acid in place of N-methylindole-2-carboxylic acid.
$^1$H NMR
FAB-MS, m/e 508 (MH$^+$)

| Analysis Calc. for $C_{26}H_{33}N_7O_4 \cdot 1.3HCl \cdot H_2O$; | | |
|---|---|---|
| | C 54.50, | H 6.39, | N 17.11; |
| Found; | C 54.85, | H 6.14, | N 16.74. |

EXAMPLE 4

Preparation of N-(3-pyridylacetyl)-D-phenylalanyl-L-prolinyl-L-arginine Aldehyde Hydrochloride

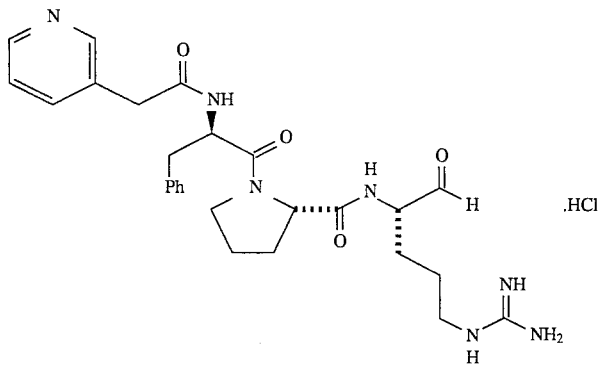

N-(α-(3-pyridyl)-acetyl)-D-Phe-Pro-Arg-H·HCl

By methods substantially equivalent to those described in Example 1-C, 1-D, 1-H and 1-I, 2.2 g of N-(α-(3-pyridyl)-acetyl)-D-Phe-Pro-Arg-H·HCl hydrate was prepared using α-(3-pyridyl)-acetic acid in place of N-methylindole-2-carboxylic acid. Also, the reduction of the tripeptide arginine lactam was performed using LiAl(O-t-Bu)$_3$H at −23° C., rather than LAH at −78° C.

$^1$H NMR

FAB-MS, m/e 523 (MH$^+$)

Analysis Calc. for $C_{27}H_{35}N_7O_4 \cdot 2.4HCl \cdot 3.5H_2O$;

|  | C 48.25, | H 6.66, | N 14.59, | Cl 12.66; |
|---|---|---|---|---|
| Found; | C 48.60, | H 6.34, | N 14.32, | Cl 12.86. |

Boc-D-Cha-OH in place of Boc-D-Phe-OH. Also, the tripeptide arginine lactam was reduced with LiAl(O-t-Bu)$_3$H at −23° C. rather than LAH at −78° C.

$^1$H NMR

FAB-MS, m/e 566 (MH$^+$)

Analysis Calc. for $C_{30}H_{43}N_7O_4 \cdot 1.2HCl$;

|  | C 59.12, | H 7.31, | N 16.09, | Cl 6.98; |
|---|---|---|---|---|
| Found; | C 59.17, | H 7.04, | N 15.88, | Cl 6.95. |

EXAMPLE 5

Preparation of N-(1-methylindolyl-2-carbonyl)-D-cyclohexylalanyl-L-prolinyl-L-arginine Aldehyde Hydrochloride

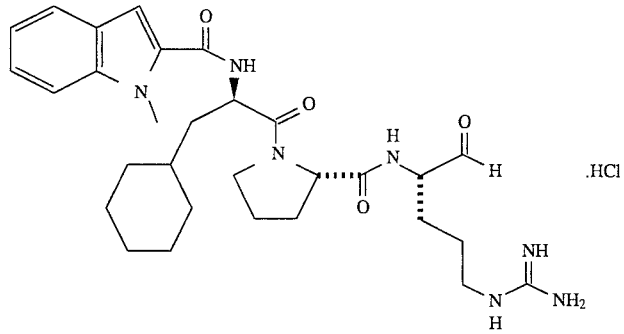

NMI-D-Cha-Pro-Arg-H·HCl

By methods substantially equivalent to those described in Example 1-A, 1-B, 1-C, 1-D, 1-H and 1-I, 2.14 g of NMI-D-Cha-Pro-Arg-H·HCl hydrate was prepared using

EXAMPLE 6

Preparation of n-(quinolinyl-2-carbonyl)-D- cyclohexylalanyl-L-prolinyl-L-arginine Aldehyde Hydrochloride N-(quinolinyl-2-carbonyl)-D-Cha-Pro-Arg-H-HCl By methods substantially equivalent to those described in example 1, 3.2 g of N-(quinoline-2-carbonyl)-D-Cha-Pro-Arg-H.HCl hydrate was prepared using Boc-D-Cha-OH in place of Boc-D-Phe-OH, and using quinoline-2-carboxylic acid in place of N-methylindole-2-carboxylic acid. Also, the tripeptide arginine lactam was reduced with LiAl(O-t-Bu)$_3$H at –23° C. rather than LAH at –78° C.

$^1$H NMR
FAB-MS, m/e 565 (MH$^+$)

| Analysis Calc. for C$_{30}$H$_{41}$N$_7$O$_4$ · 1.3HCl · 1.1H$_2$O; | | | |
|---|---|---|---|
| | C 57.11, | H 7.11, | N 15.54, Cl 7.31; |
| Found; | C 57.04, | H 6.74, | N 15.36, Cl 6.93. |

EXAMPLE 7

Preparation of N-(methylsulfonyl)-D-phenylalanyl-L-prolinyl-L-arginine Aldehyde Hydrochloride A) MeSO$_2$-D-Phe-Pro-OBzl To a stirring solution of TFA,D-Phe-Pro-OBzl (10 g, 21.4 mmol) in tetrahydrofuran (100 mL) at 0° C., was added N,N-diisopropylethylamine (15 mL, 85 mmol), followed by methanesulfonyl chloride (2 mL, 24 mmol). The cold bath was left unattended and the reaction was allowed to warm slowly to room temperature. After stirring for 24 h, the solvent was removed in vacuo and the residue was dissolved in ethyl acetate (200 mL). The ethyl acetate solution was washed twice with 1N citric acid (100 mL), once with water (100 mL), twice with saturated aqueous NaHCO$_3$ (100 mL) and once with brine (100 mL). The organic solution was then dried with MgSO$_4$, filtered and concentrated. The resulting foam was purified by chromatography over silica gel, eluting with 1:1 hexanes/ethyl acetate. The product containing fractions as judged by TLC were combined and concentrated to give 7.2 g (79%) of an off white foam.

$^1$H NMR
FD-MS, m/e 430 (M$^+$)

| Analysis Calculated for C$_{22}$H$_{26}$N$_2$O$_5$S; | | | |
|---|---|---|---|
| | C 61.38, | H 6.09, | N 6.51; |
| Found; | C 61.61, | H 6.01, | N 6.44. |

B) MeSO$_2$-D-Phe-Pro-Arg-H.HCl

By methods substantially equivalent to those described in Example 1-D, 1-H and 1-I, 310 mg of MeSO$_2$-D-Phe-Pro-Arg-H.HCl hydrate was prepared from MeSO$_2$-D-Phe-Pro-OBzl. MeSO$_2$-D-Phe-Pro-Art-H.HCl was purified by RPHPLC (98/2 (A/B), ramp to 60/40 (A/B), 360 min).

$^1$H NMR
FAB-MS, m/e 481 (MH$^+$)

| Analysis Calc. for C$_{21}$H$_{32}$N$_6$O$_5$S · HCl · H$_2$O; | | | |
|---|---|---|---|
| | C 47.14, | H 6.59, | N 15.71; |
| Found; | C 47.33, | H 6.49, | N 15.66. |

EXAMPLE 8

Preparation of N-(ethylsulfonyl)-D-phenylalanyl-L-prolinyl-L-arginine Aldehyde Hydrochloride EtSO$_2$-D-Phe-Pro-Arg-H-HCl By methods substantially equivalent to those described in Example 7, 0.5 g of EtSO$_2$-D-Phe-Pro-Arg-H.HCl hydrate was prepared using EtSO$_2$Cl in place of MeSO$_2$C$_1$. EtSO$_2$-

D-Phe-Pro-Art-H.HCl was purified by RPHPLC (98/2 (A/B), 30 min; ramp to 80/20 (A/B), 270 min).
$^1$H NMR
FAB-MS, m/e 495 (MH$^+$)

| Analysis Calc. for $C_{22}H_{34}N_6O_5S \cdot 2HCl \cdot 1.5H_2O$; | | |
|---|---|---|
| | C 44.56, | H 6.37, | N 14.17; |
| Found; | C 44.73, | H 6.41, | N 14.08. |

EXAMPLE 9

Preparation of N-(n-propylsulfonyl)-D-phenylalanyl-L-prolinyl-L-arginine Aldehyde Hydrochloride

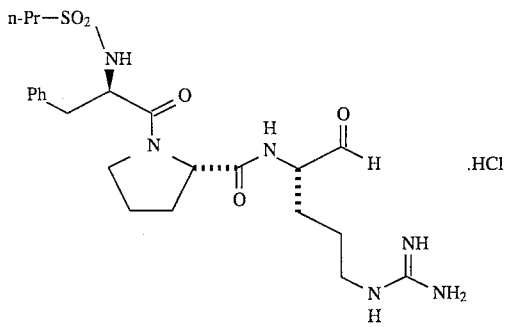

n-Pr-SO$_2$-D-Phe-Pro-Arg-H.HCl

By methods substantially equivalent to those described in Example 7, 0.47 g of n-Pr-SO$_2$-D-Phe-Pro-Arg-H.HCl hydrate was prepared using n-Pr-SO$_2$Cl in place of MeSO$_2$Cl. n-Pr-SO$_2$-D-Phe-Pro-Arg-H.HCl was purified by RPHPLC (98/2 (A/B), ramp to 60/40 (A/B), 240 min).
$^1$H NMR
FAB-MS, m/e 509 (MH$^+$)

| Analysis Calc. for $C_{23}H_{36}N_6O_5S \cdot HCl \cdot 1.5H_2O$; | | |
|---|---|---|
| | C 48.29, | H 7.05, | N 14.69; |
| Found; | C 48.00 | H 6.71 | N 14.54 |

EXAMPLE 10

Preparation of N-(n-butylsulfonyl)-D-phenylalanyl-L-prolinyl-L-arginine Aldehyde Hydrochloride

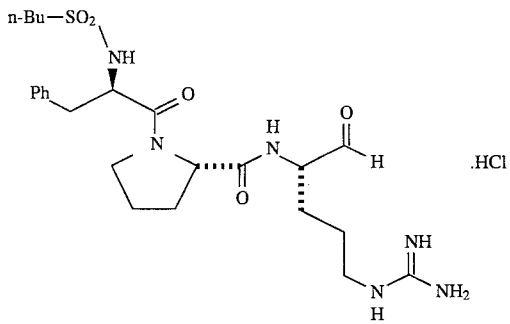

n-Bu-SO$_2$-D-Phe-Pro-Arg-H.HCl

By methods substantially equivalent to those described in Example 7, 0.94 g of n-Bu-SO$_2$-D-Phe-Pro-Arg-H.HCl was prepared using n-Bu-SO$_2$Cl in place of MeSO$_2$Cl. n-Bu-SO$_2$-D-Phe-Pro-Arg-H.HCl was purified by RPHPLC (98/2 (A/B), ramp to 60/40 (A/B), 240 min).

$^1$H NMR
FAB-MS, m/e 523 (MH$^+$)

| Analysis Calc. for $C_{24}H_{38}N_6O_5S \cdot HCl$; | | |
|---|---|---|
| | C 51.56, | H 7.03, | N 15.03; |
| Found; | C 51.65, | H 7.22, | N 14.79. |

EXAMPLE 11

Preparation of N-(isopropylsulfonyl)-D-phenylalanyl-L-prolinyl-L-arginine Aldehyde Hydrochloride

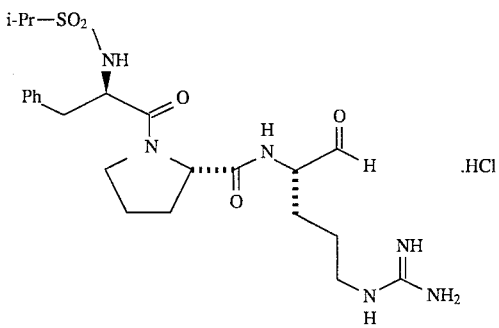

i-Pr-SO$_2$-D-Phe-Pro-Arg-H-HCl

By methods substantially equivalent to those described in Example 7, 1 g of i-Pr-SO$_2$-D-Phe-Pro-Arg-H.HCl hydrate was prepared using i-Pr-SO$_2$Cl in place of MeSO$_2$Cl. i-Pr-SO$_2$-D-Phe-Pro-Arg-H.HCl was purified by RPHPLC (98/2 (A/B), ramp to 60/40 (A/B), 240 min).
$^1$H NMR
FAB-MS, m/e 509 (MH$^+$)

| Analysis Calc. for $C_{23}H_{37}N_6O_5S \cdot HCl \cdot 1.25H_2O$; | | |
|---|---|---|
| | C 48.67, | H 7.01, | N 14.80; |
| Found; | C 48.83, | H 6.85, | N 14.91. |

EXAMPLE 12

Preparation of N-(dimethylaminosulfonyl)-D-phenylalanyl-L-prolinyl-L-arginine Aldehyde Hydrochloride

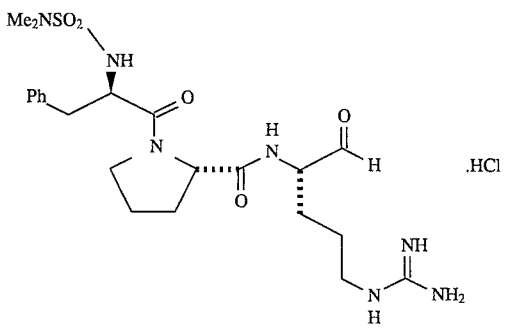

Me$_2$NSO$_2$-D-Phe-Pro-Arg-H.HCl

By methods substantially equivalent to those described in Example 7, 1.1 g of Me$_2$NSO$_2$-D-Phe-Pro-Arg-H.HCl hydrate was prepared using Me$_2$NSO$_2$Cl in place of MeSO$_2$Cl. Also, the tripeptide arginine lactam was reduced with LiAl(O-t-Bu)$_3$H at −23° C. rather than LAH at −78° C. Me$_2$NSO$_2$-D-Phe-Pro-Arg-H-HCl was purified by RPHPLC (98/2 (A/B), ramp to 60/40 (A/B), 240 min).

¹H NMR
FAB-MS, m/e 510 (MH⁺)

| Analysis Calc. for C₂₂H₃₅N₇O₅S · HCl · H₂O; | | | |
|---|---|---|---|
| | C 44.27, | H 6.57, | N 16.08, | Cl 11.28; |
| Found; | C 44.55, | H 5.89, | N 16.05, | Cl 10.82. |

EXAMPLE 13

Preparation of N-(phenylsulfonyl)-D-phenylalanyl-L-prolinyl-L-arginine Aldehyde Hydrochloride

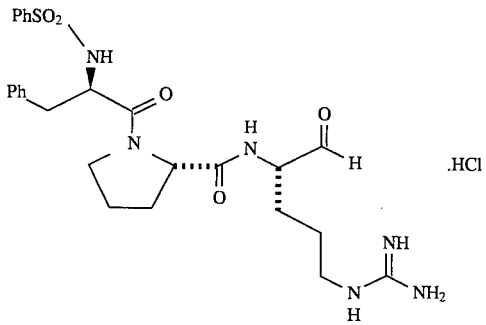

PhSO₂-D-Phe-Pro-Arg-H.HCl

By methods substantially equivalent to those described in Example 7, 2.3 g of PhSO₂-D-Phe-Pro-Arg-H.HCl dihydrate was prepared using PhSO₂Cl in place of MeSO₂Cl. Also, the tripeptide arginine lactam was reduced with LiAl(O-t-Bu)₃H at −23° C. rather than LAH at −78° C.

¹H NMR
FAB-MS, m/e 543 (MH⁺)

| Analysis Calc. for C₂₆H₃₄N₆O₅S · 2HCl · 2.1H₂O; | | | |
|---|---|---|---|
| | C 50.01, | H 6.39, | N 13.46, | Cl 6.81; |
| Found; | C 49.88, | H 6.16, | N 13.10, | Cl 6.63. |

EXAMPLE 14

Preparation of N-(2,4-difluoroyphenylsulfonyl)-D-phenylalanyl-L-prolinyl-L-arginine Aldehyde Hydrochloride

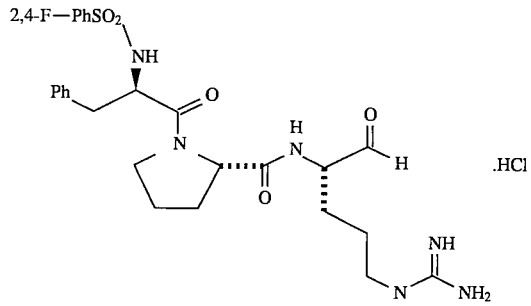

2,4-F-PhSO₂-D-Phe-Pro-Arg-H-HCl

By methods substantially equivalent to those described in Example 7, 0.94 g of 2,4-difluorophenyl-SO₂-D-Phe-Pro-Arg-H.HCl hydrate was prepared using 2,4-difluorophenyl-SO₂Cl in place of MeSO₂Cl. Also, the tripeptide arginine lactam was reduced with LiAl(O-t-Bu)₃H at −23° C. rather than LAH at −78° C. 2,4-F-PhSO₂-D-Phe-Pro-Arg-H.HCl was purified by RPHPLC (95/5 (A/B), ramp to 70/30 (A/B), 240 min).

¹H NMR
FAB-MS, m/e 579 (MH⁺)
Exact Mass Calc'd for C₂₆H₃₃N₆O₅F₂S, 579.220122; Found, 579.218900

| Analysis Calculated for C₂₆H₃₂N₆O₅F₂S · 1.5HCl · H₂O; | | |
|---|---|---|
| | C 47.95 | H 5.49 | N 12.90; |
| Found; | C 47.92 | H 5.19 | N 12.78. |

EXAMPLE 15

Preparation of N-(2,5-dimethoxyphenylsulfonyl)-D-phenylalanyl-L-prolinyl-L-arginine Aldehyde Hydrochloride

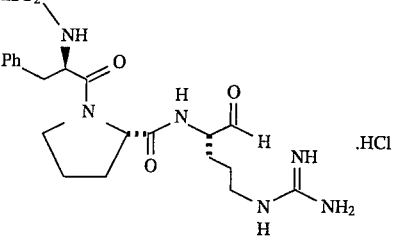

2,5-(MeO)₂-PhSO₂-D-Phe-Pro-Arg-H-HCl

By methods substantially equivalent to those described in Example 7, 5 g of 2,5-dimethoxyphenyl-SO₂-D-Phe-Pro-Arg-H-HCl hydrate was prepared using 2,5-dimethoxyphenyl-SO₂Cl in place of MeSO₂Cl. Also, the tripeptide arginine lactam was reduced with LiAl(O-t-Bu)₃H at −23° C. rather than LAH at −78° C.

¹H NMR
FAB-MS, m/e 603 (MH⁺)

| Analysis Calc. for C₂₈H₃₈N₆O₇S · 1.5HCl · H₂O; | | |
|---|---|---|
| | C 49.79, | H 6.19, | N 12.44; |
| Found; | C 50.32, | H 6.17, | N 12.05. |

EXAMPLE 16

Preparation of N-(3,5-dimethyl-4-isoxazolylsulfonyl)-D-phenylalanyl-L-prolinyl-L-arginine Aldehyde Hydrochloride

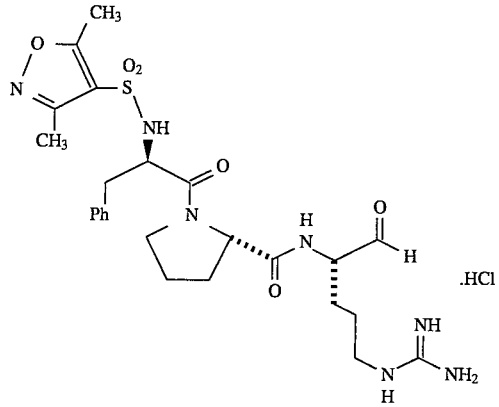

3,5-Me-4-isoxazolyl-SO₂-D-Phe-Pro-Arg-H.HCl

By methods substantially equivalent to those described in Example 7, 0.43 g of 3,5-dimethyl-4-isoxazolyl-SO₂-D-Phe-Pro-Arg-H.HCl hydrate was prepared using 3,5-dimethyl-4-isoxazolyl-SO₂Cl in place of MeSO₂Cl. 3,5-dimethyl-4-isoxazolyl-SO₂-D-Phe-Pro-Arg-H.HCl was purified by RPHPLC (98/2 (A/B), ramp to 65/35 (A/B), 240 min).

¹H NMR

FAB-MS, m/e 562 (MH⁺)

| Analysis Calc. for C₂₅H₃₅N₇O₆S•1.4HCl•H₂O; | C 47.61, | H 6.14, | N 15.55; |
|---|---|---|---|
| Found; | C 47.97, | H 5.91, | N 15.22. |

EXAMPLE 17

Preparation of N-(8-quinolinylsulfonyl)-D-phenylalanyl-L-prolinyl-L-arginine Aldehyde Hydrochloride 8-Quinolyl-SO₂-D-Phe-Pro-Arg-H.HCl By methods substantially equivalent to those described in Example 7, 0.050 g of 8-quinolyl-SO₂-D-Phe-Pro-Arg-H.HCl was prepared using 8-quinolyl-SO₂Cl in place of MeSO₂Cl. 8-quinolyl-SO₂-D-Phe-Pro-Arg-H.HCl was purified by RPHPLC (95/5 (A/B), ramp to 70/30 (A/B), 240 min).

¹H NMR

FAB-MS, m/e 594 (MH⁺)

Exact Mass Calc'd for C₂₉H₃₆N₇O₅S, 594.2499; Found, 594.2505.

| Analysis Calculated for C₂₉H₃₅N₇O₅S•4HCl•2H₂O; | C 44.91 | H 5.59 | N 12.64; |
|---|---|---|---|
| Found; | C 44.97 | H 5.09 | N 10.32. |

EXAMPLE 18

Preparation of N-(4-carboxyphenylsulfonyl)-D-phenylalanyl-L-prolinyl-L-arginine Aldehyde Hydrochloride

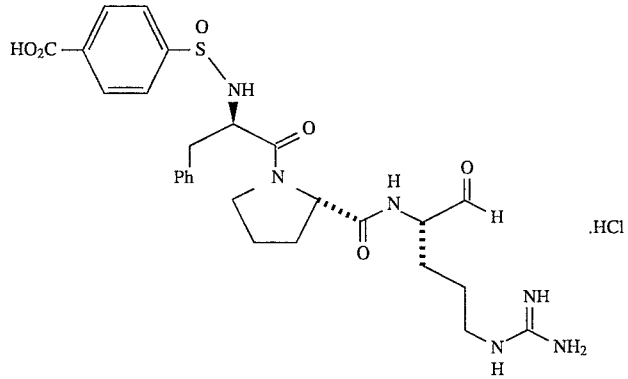

A) 4-(BzlO₂C)-C₆H₄SO₂Cl

To a solution of p-chlorosulfonylbenzoic acid (25 g, 113 mmol) in dichloromethane (500 mL) and dimethyl formamide (150 mL), was added oxalyl chloride (12.3 mL, 141 mmol). After stirring for 2 h, the solvents were removed in vacuo.

The residue was then mixed with benzyl alcohol (95 mL) at room temperature, which caused the development of heat. After the heat dissipated, the mixture was partitioned between water and ethyl acetate. The layers were separated and the aqueous phase was extracted twice with ethyl acetate. The combined organic phase was dried with Na₂SO₄, filtered and then concentrated to about ¼ original volume, then refrigerated over night. The next morning, the precipitate was filtered and dried to give 2.8 g (8%) of the named product.

¹H NMR

FD-MS, m/e 310 (M⁺)

B) Cbz-D-Phe-Pro-O-t-Bu

By a method substantially equivalent to that described in example 1-A, 29 g (90%) of Cbz-D-Phe-Pro-O-t-Bu was prepared, using Cbz-D-Phe-OH in place of Boc-D-Phe-OH and HCl, Pro-0-t-Bu in place of HCl.Pro-OBzl.

¹H NMR

FD-MS, m/e 452 (M⁺)

C) D-Phe-Pro-O-t-Bu

To a solution of Cbz-D-Phe-Pro-O-t-Bu (29 g, 64 mmol) in ethanol (500 mL) was added 5% Pd/C (14.5 g). The mixture was shaken on a hydrogenation apparatus for 16 h under 60 psi H₂. The solution was then filtered through a pad of Celite® and concentrated in vacuo to give 17.5 g (86%) of thick oil.

¹H NMR

FD-MS, m/e 319 (MH⁺)

| Analysis Calculated for C₁₈H₂₆N₂O₃; | C 67.90, | H 8.23, | N 8.80; |
|---|---|---|---|
| Found; | C 67.66, | H 8.19, | N 8.67. |

D) 4-(BzlO₂C)-C₆H₄SO₂-D-Phe-Pro-O-t-Bu

By a method substantially equivalent to that described in Example 7-A, 11.3 g (50%) of 4-(BzlO₂C)-C₆H₄SO₂-D-

Phe-Pro-O-t-Bu was prepared, using 4-(BzlO$_2$C)-C$_6$H$_4$SO$_2$Cl in place of MeSO$_2$Cl and D-Phe-Pro-O-t-Bu in place of TFA.D-Phe-Pro-OBzl.

FD-MS, m/e 592 (M$^+$)

E) 4-(BzlO$_2$C)-C$_6$H$_4$SO$_2$-D-Phe-Pro-OH 4-(BzlO$_2$C)-C$_6$H$_4$SO$_2$-D-Phe-Pro-O-t-Bu (11.3 g, 19 mmol) was dissolved in trifluoroacetic acid (100 mL) and anisole (5 mL). After stirring for 2 h, the solvent was removed by rotary evaporation. The residue was partitioned between diethyl ether (300 mL) and saturated aqueous NaHCO$_3$ (300 mL). The layers were separated and the aqueous phase was acidified to pH 2 with 5N HCl, then extracted three times with ethyl acetate (200 mL). The combined ethyl acetate extracts were dried (MgSO$_4$), filtered and concentrated in vacuo to give 6.5 g (64%) of a thick, light brown oil.

FD-MS, m/e 538 (MH$^+$)

F) 4-(HO$_2$C)-C$_6$H$_4$SO$_2$-D-Phe-Pro-Arg-H.HCl

By methods substantially equivalent to those described in Example 1-H and 1-I, 0.8 g of 4-(HO$_2$C)-C$_6$H$_4$SO$_2$-D-Phe-Pro-Arg-H.HCl hydrate was prepared. The tripeptide arginine lactam was reduced with LiAl(O-t-Bu)$_3$H at $-23°$ C. rather than LAH at $-78°$ C. The product was contaminated with tripeptide arginine alcohol which could not be removed by RPHPLC.

$^1$H NMR
FAB-MS, m/e 587 (MH$^+$)

| Analysis Calculated for C$_{27}$H$_{34}$N$_6$O$_7$S•1.3HCl•H$_2$O | C 49.73 | H 5.77 | N 12.89 |
|---|---|---|---|
| Found | C 49.60 | H 5.76 | N 12.93 |

EXAMPLE 19

Preparation of N-(2-thiazolylsulfonyl)-D-phenylalanyl-L-prolinyl-L-arginine Aldehyde Hydrochloride

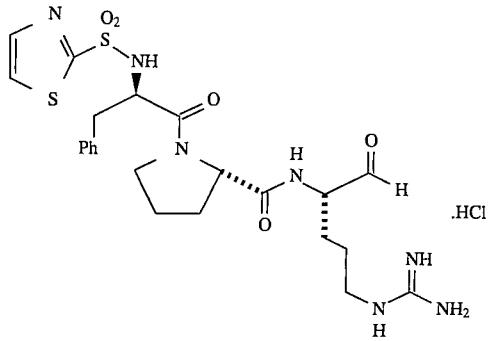

A) 2-Thiazolyl-SO$_2$Cl

To a solution of thiazole (10 g, 118 mmol) in tetrahydrofuran (600 mL) at $-78°$ C. was slowly added a solution of n-butyl lithium, 1.6M in hexanes (73 mL, 118 mmol). After 1 h, SO$_2$ (g) was bubbled through the solution until an aliquot was acidic to moist pH paper. The cold bath was then removed and the solution was allowed to warm to room temperature. The solution was then poured into hexanes (1.5 L) and the resulting precipitate was filtered and dried to give 16.7 g of a light yellow solid.

The solid (10 g) was then suspended in dichloromethane (60 mL), cooled to 0° C., and treated with N-chlorosuccinimide (8.6 g, 64.5 mmol). After stirring for 2 h, the solution was filtered, and the filtrate was concentrated in vacuo to give 6.2 g of a yellow oil. The oil was then dissolved in diethyl ether, filtered and concentrated in vacuo to give 4.4 g (34%) of oil.

FD-MS, m/e 183 (M$^+$)

SB) 2-Thiazolyl-SO$_2$-D-Phe-Pro-Arg(Cbz)lactam

By methods substantially equivalent to those described in Example 7-A, 1-D, and 1-H, 7.7 g of 2-thiazolyl-SO$_2$-D-Phe-Pro-Arg(Cbz)lactam was prepared using 2-thiazolyl-SO$_2$Cl in place of MeSO$_2$Cl.

$^1$H NMR
FD-MS, m/e 682 (M$^+$)

| Analysis Calculated for C$_{31}$H$_{35}$N$_7$O$_7$S; | C 54.61, | H 5.17, | N 14.38; |
|---|---|---|---|
| Found; | C 54.38, | H 5.27, | N 14.09. |

C) 2-Thiazolyl-SO$_2$-D-Phe-Pro-Arg-H-HCl

2-Thiazolyl-SO$_2$-D-Phe-Pro-Arg(Cbz)lactam was reduced using LAH by a method substantially equivalent to that described in Example 1-I. The Cbz protecting group was then removed by treatment with liquid HF (10 mL) and anisole (1.0 mL) in a Teflon®/Kel-F® apparatus at 0° C. for 1 hour to yield after evaporation of HF and precipitation with Et$_2$O 1.1 g of crude 2-thiazolyl-SO$_2$-D-Phe-Pro-Arg-H.HF. The crude product was then purified by RPHPLC (98/2 (A/B), 40 min; ramp to 80/20 (A/B), 280 min) to yield 280 mg of pure 2-thiazolyl-SO$_2$-D-Phe-Pro-Arg-H.HCl $^1$H NMR
FAB-MS, m/e 550 (MH$^+$)

| Analysis Calc. for C$_{23}$H$_{31}$N$_7$O$_5$S$_2$•1.1HCl•H$_2$O; | C 45.45, | H 5.65, | N 16.13, | Cl 6.42; |
|---|---|---|---|---|
| Found; | C 45.29, | H 5.35, | N 15.86, | Cl 6.72. |

EXAMPLE 20

Preparation of N-(ethylsulfonyl)-D-phenylglycinyl-L-prolinyl-L-arginine Aldehyde Hydrochloride

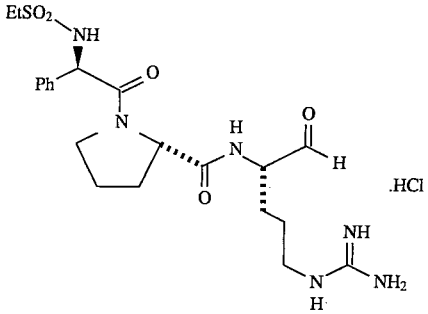

EtSO$_2$-D-Phg-Pro-Arg-H.HCl

By methods substantially equivalent to those described in Examples 1-A, 1-B, 7-A, 1-D, 1-H and 1-I, using Boc-D-Phg-OH in place of Boc-D-Phe-OH, EtSO$_2$Cl in place of MeSO$_2$Cl, and LiAl(O-t-Bu)$_3$H at $-23°$ C. in place of LAH at $-78°$ C., 450 mg of EtSO$_2$-D-Phg-Pro-Arg-H.HCl hydrate was prepared. EtSO$_2$-D-Phg-Pro-Arg-H.HCl Pro-Arg-H.HCl was purified by RPHPLC (98/2 (A/B), ramp to 60/40 (A/B), 240 min).

$^1$H NMR
FAB-MS, m/e 481 (MH$^+$)

| Analysis Calc. for C$_{21}$H$_{32}$N$_6$O$_5$S•HCl•1.5H$_2$O; | C 46.36, | H 6.67, | N 15.45; |
|---|---|---|---|
| Found; | C 46.66, | H 6.35, | N 15.31. |

EXAMPLE 21

Preparation of N-(ethylsulfonyl)-D-cyclohexylalanyl-L-prolinyl-L-arginine Aldehyde Hydrochloride

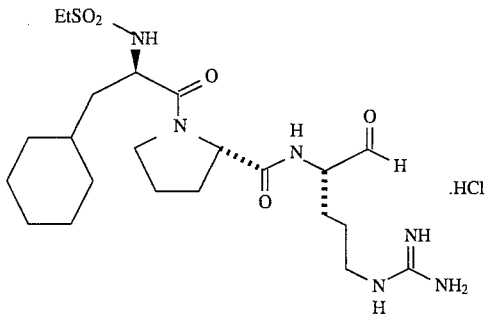

EtSO$_2$-D-Cha-Pro-Arg-H.HCl

By methods substantially equivalent to those described in Example 1-A, 1-B, 7-A, 1-D, 1-H and 1-I, using Boc-D-Cha-OH in place of Boc-D-Phe-OH, and EtSO$_2$Cl in place of MeSO$_2$Cl, 1.3 g of EtSO$_2$-D-Cha-Pro-Arg-H.HCl was prepared. EtSO$_2$-D-Cha-Pro-Arg-H.HCl was purified by RPHPLC (98/2 (A/B), ramp to 60/40 (A/B), 240 min).

$^1$H NMR
FAB-MS, m/e 501 (MH$^+$)

| Analysis Calculated for C$_{22}$H$_{40}$N$_6$O$_5$S•1.8HCl; | C 46.66 | H 7.44 | N 14.84; |
|---|---|---|---|
| Found; | C 47.05 | H 7.05 | N 14.65. |

EXAMPLE 22

Preparation of N-(ethylsulfonyl)-D-cyclohexylglycinyl-L-prolinyl-L-arginine Aldehyde Hydrochloride

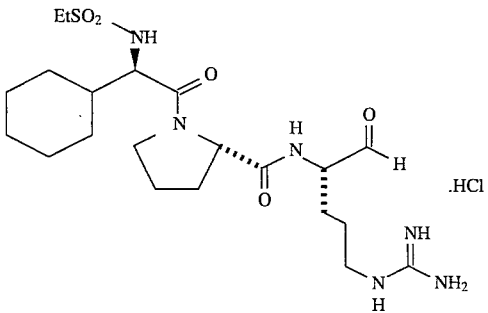

A. HCl.D-Chg-OMe

HCl (g) was bubbled through a suspension of D-Chg-OH.HCl (37.8 g, 240 mmol) in methanol (750 mL) for about 20 min. During this time, all of the solid went into solution. The solution was allowed to stir for 48 h, and then diethyl ether (1.5 L) was added. The resulting precipitate was filtered and dried to give 32.1 g (64%) of a light brown solid.

FD-MS, m/e 172 (MH$^+$)

B. EtSO$_2$-D-Chg-OMe

By a method substantially equivalent to that described in Example 7-A, 14.2 g (75%) of EtSO$_2$-D-Chg-OMe was prepared from HCl.D-Chg-OMe, using EtSO$_2$Cl in place of MeSO$_2$Cl.

$^1$H NMR
FD-MS, m/e 263 (M$^+$)

| Analysis Calculated for C$_{11}$H$_{21}$NO$_4$S; | C 50.17 | H 8.04, | N 5.32; |
|---|---|---|---|
| Found; | C 50.07, | H 8.13, | N 5.31. |

C. EtSO$_2$-D-Chg-OH

By a method substantially equivalent to that described in Example 1-D, 12.5 g (94%) of EtSO$_2$-D-Chg-OH was prepared from EtSO$_2$-D-Chg-OMe.

$^1$H NMR
FD-MS, m/e 250 (MH$^+$)

| Analysis Calculated for C$_{10}$H$_{19}$NO$_4$S; | C 48.17, | H 7.68, | N 5.62; |
|---|---|---|---|
| Found: | C 48.40, | H 7.93, | N 5.23. |

D. EtSO$_2$-D-Chg-Pro-Arg-H.HCl

By methods substantially equivalent to those described in Examples 1-A, 1-D, 1-H and 1-I, 0.25 g of EtSO$_2$-D-Chg-Pro-Art-H.HCl hydrate was prepared using EtSO$_2$-D-Chg-OH in place of Boc-D-Phe-OH. EtSO$_2$-D-Chg-Pro-Arg-H.HCl hydrate was purified by RPHPLC (98/2 (A/B), 30 min; ramp to 75/25 (A/B), 270 min).

$^1$H NMR
FAB-MS, m/e 487 (MH$^+$)

| Analysis Calculated For C$_{21}$H$_{38}$N$_6$O$_6$S•1.5HCl•H$_2$O | C 45.09 | H 7.48 | N 15.02 |
|---|---|---|---|
| Found | C 44.76 | H 7.27 | N 15.02 |

EXAMPLE 23

Preparation of N-(acetyl)-D-phenylalanyl-L-prolinyl-L-arginine Aldehyde Hydrochloride

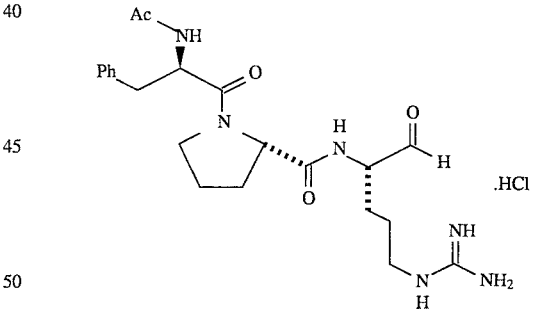

Ac-D-Phe-Pro-Arg-H.HCl

By methods substantially equivalent to those described in Example 7, using acetyl chloride in place of MeSO$_2$Cl, 210 mg of Ac-D-Phe-Pro-Arg-H.HCl dihydrate was prepared. Ac-D-Phe-Pro-Arg-H.HCl was purified by RPHPLC (95/5 (A/B), 80 min; ramp to 75/25 (A/B), 320 min; hold to 360 min).

$^1$H NMR
FAB-MS, m/e 445 (MH$^+$)

| Analysis Calc. for C$_{22}$H$_{32}$N$_6$O$_4$•2HCl•2H$_2$O; | C 47.74, | H 6.92, | N 15.18; |
|---|---|---|---|
| Found; | C 47.40, | H 6.83, | N 14.88. |

EXAMPLE 24

Preparation of N-(methoxyacetyl)-D-phenylalanyl-L-prolinyl-L-arginine Aldehyde Hydrochloride

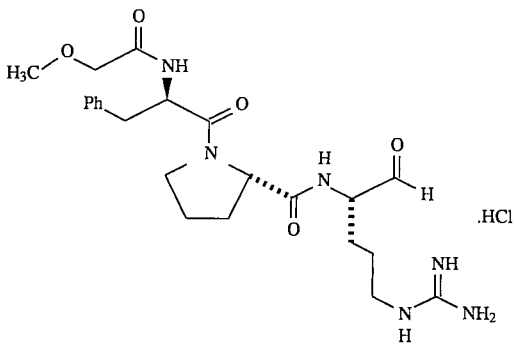

CH₃OCH₂CO-D-Phe-Pro-Arg-H.HCl

By methods substantially equivalent to those described in Example 7, using CH₃OCH₂(CO)Cl in place of MeSO₂Cl, 110 mg of CH₃OCH₂CO-D-Phe-Pro-Arg-H.HCl was prepared. CH₃OCH₂CO-D-Phe-Pro-Arg-H.HCl was purified by RPHPLC (95/5 (A/B), 80 min; ramp to 75/25 (A/B), 320 min; hold to 360 min).

¹H NMR
FAB-MS, m/e 475 (MH⁺)

| Analysis Calc. for C₂₃H₃₄N₆O₅•HCl; | C 54.06, | H 6.90, | N 16.44, | Cl 6.94; |
|---|---|---|---|---|
| Found; | C 54.33, | H 6.69, | N 16.54, | Cl 6.94. |

EXAMPLE 25

Preparation of N-(trifluoroacetyl)-D-phenylalanyl-L-prolinyl-L-arginine Aldehyde Hydrochloride

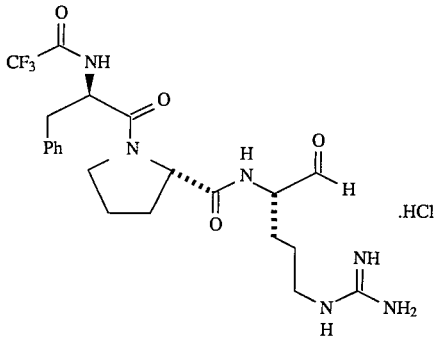

CF₃CO-D-Phe-Pro-Arg-H.HCl

By methods substantially equivalent to those described in Example 7, using trifluoroacetic anhydride in place of MeSO₂Cl, 3.6 mg of CF₃CO-D-Phe-Pro-Arg-H.HCl ethanolate was prepared.

¹H NMR
FAB-MS, m/e 499 (MH⁺)

| Analysis Calc. for C₂₂H₂₉N₆O₄F₃•1.5HCl•H₂O•EtOH; | C 46.42, | H 6.44, | N 13.59; |
|---|---|---|---|
| Found; | C 46.32, | H 6.19, | N 13.70. |

EXAMPLE 26

Preparation of N-(phenylacetyl)-D-phenylalanyl-L-Prolinyl-L-Arginine Aldehyde Hydrochloride

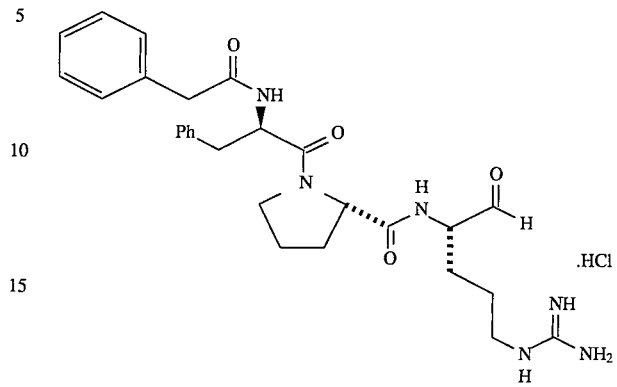

PhCH₂CO-D-Phe-Pro-Arg-H.HCl

By methods substantially equivalent to those described in Example 7, using phenylacetyl chloride in place of MeSO₂Cl, 3.5 g of PhCH₂CO-D-Phe-Pro-Arg-H.HCl was prepared.

¹H NMR
FAB-MS, m/e 521 (MH⁺)

| Analysis Calc. for C₂₈H₃₆N₆O₄•1.2HCl•H₂O•0.5EtOH; | | |
|---|---|---|
| | C 57.53, | H 7.03, | N 13.88; |
| Found; | C 57.63, | H 6.66, | N 13.52. |

EXAMPLE 27

Preparation of N-(cylohexoyl)-D-phenylalanyl-L-Prolinyl-L-Arginine Aldehyde Hydrochloride

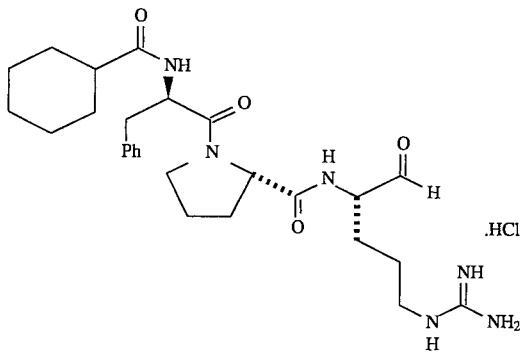

cyclohexyl-CO-D-Phe-Pro-Arg-H.HCl

By methods substantially equivalent to those described in Example 7, using cyclohexane carbonyl chloride in place of MeSO₂Cl, 5.3 g of cyclohexyl-CO-D-Phe-Pro-Arg-H.HCl was prepared.

¹H NMR
FAB-MS, m/e 513 (MH⁺)

| Analysis Calc. for C₂₇H₄₀N₆O₄•HCl; | | |
|---|---|---|
| | C 59.06, | H 7.53, | N 15.31; |
| Found; | C 59.00, | H 7.34, | N 15.07. |

EXAMPLE 28

Preparation of N-(acetyl)-D-cyclohexylalanyl-L-Prolinyl-L-Arginine Aldehyde Hydrochloride

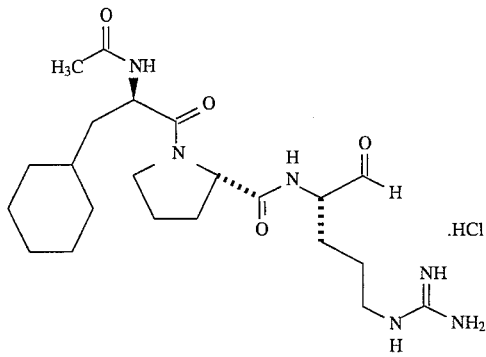

Ac-D-Cha-Pro-Arg-H.HCl

By methods substantially equivalent to those described in Examples 1-A, 1-B, 7-A, 1-D, 1-H and 1-I, using Boc-D-Cha-OH in place of Boc-D-Phe-OH, and using acetyl chloride in place of $MeSO_2Cl$, 0.62 g of Ac-D-Cha-Pro-Arg-H.HCl was prepared. Ac-D-Cha-Pro-Arg-H.HCl was purified by RPHPLC (95/5 (A/B) ramp to 70/30 (A/B), 240 min).

$^1$H NMR
FAB-MS, m/e 451 (MH$^+$)

| Analysis Calc. for $C_{22}H_{38}N_6O_4 \cdot 2HCl \cdot 0.5H_2O$; | | | |
|---|---|---|---|
| | C 49.62, | H 7.76, | N 15.78; |
| Found; | C 49.63, | H 7.61, | N 15.81. |

EXAMPLE 29

Preparation of N-(4-di-n-propylamino sulfonylbenzoyl)-D-phenylalanyl-L-Prolinyl-L-Arginine Aldehyde Hydrochloride

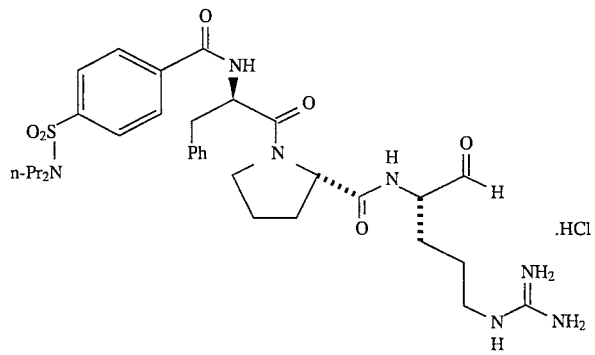

A. 4-(n-Pr$_2$NSO$_2$)-C$_6$H$_4$CO-D-Phe-Pro-OBzl

To a solution of 4-(n-Pr$_2$NSO$_2$)-C$_6$H$_4$COOH (2.5 g, 8.8 mmol) in dichloromethane (100 mL) was added TFA.D-Phe-Pro-OBzl (4.1 g, 8.8 mmol), prepared substantially according to Example 1-B, N,N-diisopropylethylamine (8.0 mL, 44 mmol), and HOBT (1.2 g, 8.8 mmol), followed by 1-(3-dimethylaminopropyl)-3-ethylcarbodiimide.HCl (1.9 g, 9.6 mmol). After stirring for 16 h, the solvents were removed in vacuo and the residue was dissolved in ethyl acetate. The organic solution was washed twice with 1N citric acid, twice with saturated aqueous NaHCO$_3$, twice with water and once with brine. The ethyl acetate was then removed in vacuo and the residue was chromatographed over silica gel, eluting with 1:1 ethyl acetate:hexanes. The product containing fractions as judged by TLC were combined and concentrated in vacuo to give 3.32 g (61%) of white foam.

$^1$H NMR
FD-MS, m/e 619 (M$^+$)

| Analysis Calculated for $C_{34}H_{41}N_3O_6S$; | | | |
|---|---|---|---|
| | C 65.89, | H 6.67, | N 6.78; |
| Found; | C 65.79, | H 6.86, | N 6.55. |

B. 4-(n-Pr$_2$NSO$_2$)-C$_6$H$_4$CO-D-Phe-Pro-Arg-H.HCl

By methods substantially equivalent to those described in Examples 1-D, 1-H and 1-I, 1.4 g of 4-(n-Pr$_2$NSO$_2$)-C$_6$H$_4$CO-D-Phe-Pro-Arg-H.HCl was prepared from 4-(n-Pr$_2$NSO$_2$)-C$_6$H$_4$CO-D-Phe-Pro-OBzl, using LiAl(O-t-Bu)$_3$H at −23° C. in place of LAH at −78° C. 4-(n-Pr$_2$NSO$_2$)-C$_6$H$_4$CO-D-Phe-Pro-Arg-H.HCl was purified by RPHPLC (95/5 (A/B) ramp to 60/40 (A/B), 240 min).

$^1$H NMR
FAB-MS, m/e 670 (MH$^+$)

| Analysis Calc. for $C_{33}H_{47}N_7O_6S \cdot HCl$; | | | |
|---|---|---|---|
| | C 56.12, | H 6.85, | N 13.88, | Cl 5.02; |
| Found; | C 56.40, | H 6.81, | N 13.78, | Cl 5.06. |

EXAMPLE 30

Preparation of N-(cyclohexylmethyl)-D-phenylalanyl-L-Prolinyl-L-Arginine Aldehyde Hydrochloride

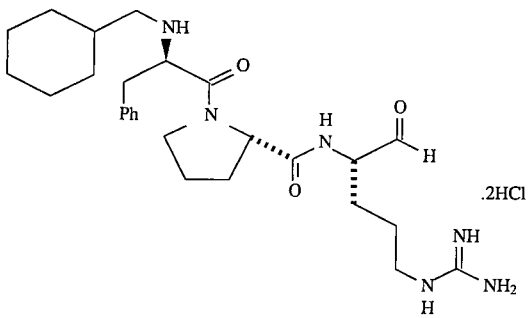

A. cyclohexyl-$CH_2$-D-Phe-Pro-O-t-Bu

To a solution of Cbz-D-Phe-Pro-O-t-Bu (11.2 g, 24.7 mmol) and cyclohexanecarboxaldehyde (4.4 mL, 37.6 mmol) in ethanol (135 mL) was added 5% Pd/C (2 g). The suspension was shaken under an atmosphere of $H_2$ (60 psi) overnight. The solution was then filtered and concentrated in vacuo. The residue was then dissolved in methanol, filtered through an acrodisc, and then concentrated in vacuo. The residue was then dissolved in diethyl ether, filtered and extracted three times with 1N citric acid. The combined aqueous acid phase was adjusted to pH 10 with 2N NaOH and extracted three times with chloroform. The combined chloroform extracts were dried over $Na_2SO_4$, filtered and concentrated in vacuo to give 6.5 g (64%) of clear oil.

$^1$H-NMR

FD-MS, m/e 415 (MH$^+$)

B. Cbz-N-cyclohexyl-$CH_2$-D-Phe-Pro-OH

To a solution of cyclohexyl-$CH_2$-D-phe-pro-O-t-Bu (6.3 g, 15.2 mmol) in dichloromethane (100 mL) at 0° C. was added N,N-diisopropylethylamine (10.4 mL, 62.6 mmol). To this stirring solution was slowly added a solution of benzyl chloroformate (3.8 mL, 16.8 mmol) in dichloromethane (25 mL). After 1.5 h, chloroform (100 mL) was added and the solution was washed three times with 1N HCl and once with water. The organic phase was then dried over $Na_2SO_4$, filtered and concentrated in vacuo.

The residue was dissolved in a solution of anisole (5 mL) in trifluoroacetic acid (50 mL) at 0° C. and allowed to stir for 5 h. The solvents were then removed in vacuo and the residue was partitioned between diethyl ether and saturated aqueous $NaHCO_3$. The diethyl ether phase was again extracted three times with saturated aqueous $NaHCO_3$ and three times with water. The combined aqueous extracts were acidified to pH 2 with 1N HCl and extracted three times with chloroform. The combined chloroform extracts were dried ($Na_2SO_4$), filtered and concentrated in vacuo to give 6.3 g (84%) of a pale yellow foam.

$^1$H NMR

FD-MS, m/e 493 (MH$^+$)

| Analysis Calculated for $C_{29}H_{36}N_2O_5$•0.15 $CHCl_3$; | C 68.58, | H 7.14, | N 5.48; |
|---|---|---|---|
| Found; | C 68.36, | H 7.21, | N 5.30. |

C. cyclohexyl-$CH_2$-D-phe-pro-Arg-H.HCl

By methods substantially equivalent to those described in Examples 1-H and 1-I, 3.4 g of cyclohexyl-$CH_2$-D-phe-pro-Arg-H.HCl dihydrate was prepared from Cbz-N-cyclohexyl-$CH_2$-D-Phe-Pro-OH.

FAB-MS, m/e 499 (MH$^+$)

| Analysis Calc. for $C_{27}H_{42}N_6O_3$.2.5HCl.2$H_2O$; | | | |
|---|---|---|---|
| | C 51.82, | H 7.81, | N 13.43; |
| Found; | C 51.94, | H 7.50, | N 13.25. |

EXAMPLE 31

Preparation of N-methyl-D-cyclohexylalanyl-L-Prolinyl-L-Arginine Aldehyde Hydrochloride

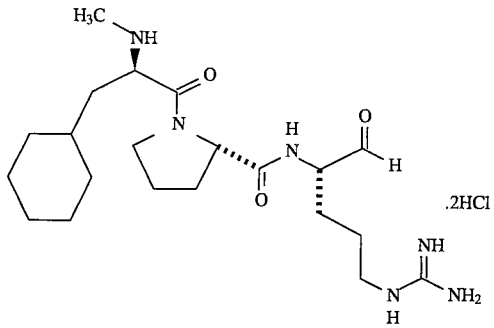

A. Cbz-D-Cha-Pro-OH

By a method substantially equivalent to that described in Example 18-E, 16.6 g (86%) of Cbz-D-Cha-Pro-OH was prepared from Cbz-D-Cha-Pro-O-t-Bu.

FD-MS, m/e 403 (MH$^+$)

| Analysis Calculated for $C_{22}H_{30}N_2O_5$; | | | |
|---|---|---|---|
| | C 65.65, | H 7.51, | N 6.96; |
| Found; | C 66.10, | H 7.44, | N 7.55. |

B. Cbz-N-Me-D-Cha-Pro-OH

To a suspension of KH (19.3 g, 25% suspension in oil, mmol) in tetrahydrofuran (100 mL) at 0° C. was slowly added (over 25 min) a solution of Cbz-D-Cha-Pro-OH (16.8 g, 41.7 mmol) in tetrahydrofuran (50 mL). During this addition period the internal temperature was monitored and maintained at less than 10° C. To this solution was then slowly added a solution of methyl iodide (5 mL, 80 mmol) and 18-crown-6 (661 mg, 2.5 mmol), again maintaining the internal temperature below 10° C. After 2 h acetic acid (10 mL) was added dropwise, followed by water (10 mL). The solution was then poured into cold water and the pH was adjusted to 9 with 2N NaOH. The aqueous base was washed twice with diethyl ether and then acidified to pH 2 with conc. HCl and extracted four times with chloroform. The chloroform extracts were combined, dried over $Na_2SO_4$, filtered and concentrated in vacuo to afford 15.7 g (90%) of a pale yellow solid.

$^1$H-NMR

FD-MS, m/e 417 (MH$^+$)

| Analysis Calculated for $C_{23}H_{32}N_2O_5$; | C 66.33, | H 7.74, | N 6.73; |
|---|---|---|---|
| Found; | C 66.49, | H 7.86, | N 6.67. |

C. Me-D-Cha-Pro-Arg-H.HCl

By methods substantially equivalent to those described in Examples 1-H and 1-I, using LiAl(O-t-Bu)3H at −23° C. in place of LAH at −78° C., 2.2 g of Me-D-Cha-Pro-Arg- H.HCl dihydrate was prepared from Cbz-N-Me-D-Cha-Pro-OH.

$^1$H NMR

FAB-MS, m/e 423 (MH$^+$)

| Analysis Calc. for $C_{21}H_{38}N_6O_3 \cdot 2HCl \cdot 2H_2O$; | C 47.45, | H 8.34, | N 15.81, | Cl 13.34; |
|---|---|---|---|---|
| Found; | C 47.07, | H 7.95, | N 15.61, | Cl 13.77. |

EXAMPLE 32

Preparation of N-(ethylaminocarbonyl)-D-phenylalanyl-L-Prolinyl-L-Arginine Aldehyde Hydrochloride

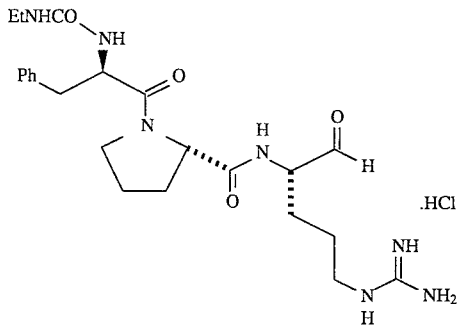

A. EtNHCO-D-Phe-Pro-OBzl

To a solution of TFA-D-Phe-Pro-OBzl (10 g, 21.4 mmol) in dichloromethane (150 mL) was added N,N-diisopropylethylamine (3.73 mL, 21.4 mmol) followed by ethyl isocyanate (1.86 mL, 23.5 mmol). After stirring for 16 h, the solution was washed three times with 1N HCl, dried over Na$_2$SO$_4$, filtered and concentrated in vacuo to give 9.7 g (107%) of white foam.

FD-MS, m/e 424 (MH$^+$)

B. EtNHCO-D-Phe-Pro-Arg-H.HCl

By methods substantially equivalent to those described in Example 1-D, 1-H and 1-I, 1.2 g of EtNHCO-D-Phe-Pro-Arg-H.HCl hydrate was prepared from EtNHCO-D-Phe-Pro-OBzl.

FAB-MS, m/e 474 (MH$^+$)

| Analysis Calc. for $C_{23}H_{35}N_7O_4 \cdot 2.1HCl \cdot H_2O$; | | | |
|---|---|---|---|
| | C 48.62, | H 6.94, | N 17.26; |
| Found; | C 48.79, | H 6.88, | N 16.90. |

EXAMPLE 33

Preparation of N-(ethoxycarbonyl)-D-phenylalanyl-L-Prolinyl-L-Arginine Aldehyde Hydrochloride

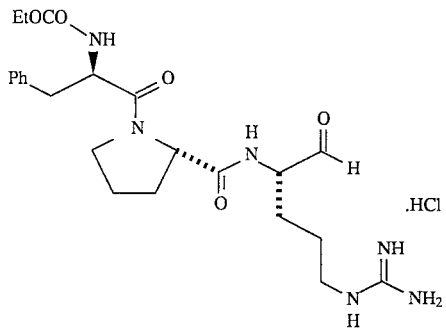

EtOCO-D-Phe-Pro-Arg-H.HCl

By methods substantially equivalent to those described in Example 7, using ethyl chloroformate in place of MeSO$_2$Cl, 2.5 g of EtOCO-D-Phe-Pro-Arg-H.HCl was prepared.

$^1$H NMR

FAB-MS, m/e 475 (MH$^+$)

| Analysis Calc. for $C_{23}H_{34}N_6O_5 \cdot 1.7HCl \cdot H_2O \cdot 0.6EtOH$; | | | |
|---|---|---|---|
| | C 49.93, | H 7.15, | N 14.43; |
| Found; | C 50.04, | H 6.76, | N 14.14. |

EXAMPLE 34

Preparation of N-(ethoxycarbonyl)-D-cyclohexylalanyl-L-Prolinyl-L-Arginine Aldehyde Hydrochloride

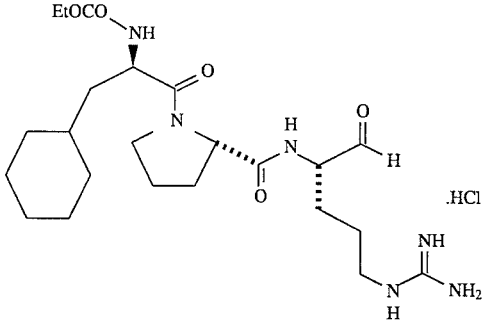

EtOCO-D-Cha-Pro-Arg-H.HCl

By methods substantially equivalent to those described in Examples 1-A, 1-B, 7-A, 1-D, 1-H and 1-I, using ethyl chloroformate in place of MeSO$_2$Cl and using Boc-D-Cha-OH in place of Boc-D-Phe-OH, 0.6 g of EtOCO-D-Cha-Pro-Arg-H.HCl hydrate was prepared. EtOCO-D-Cha-Pro-Arg-H.HCl was purified by RPHPLC (95/5 (A/B) ramp to 60/40 (A/B), 240 min).

$^1$H NMR

FAB-MS, m/e 481 (MH$^+$)

| Analysis Calc. for $C_{23}H_{40}N_6O_5 \cdot 2.8HCl \cdot H_2O$; | | | |
|---|---|---|---|
| | C 45.99 | H 7.52 | N 13.99 |
| Found; | C 45.86 | H 7.15 | N 13.70 |

EXAMPLE 35

Preparation of N-(carboxymethyl)-D-phenylalanyl-L-Prolinyl-L-Arginine Aldehyde Hydrochloride

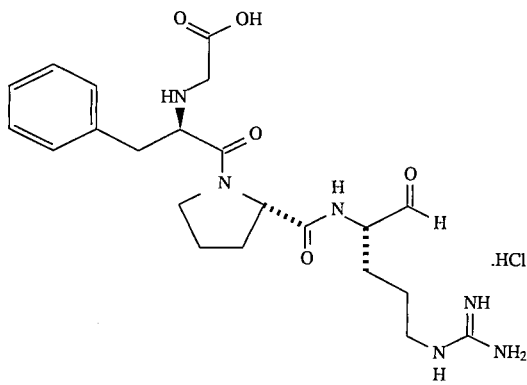

A) Preparation of D-Phe-Pro-OBn.HCl

To a suspension of Boc-D-phenylalanine (42.4 g, 160 mmol) in methylene chloride was added proline benzyl ester hydrochloride (38.7 g, 160 mmol), 1-hydroxybenzotriazole hydrate (21.6 g, 160 mmol) and diisopropylethylamine (83 mL, 480 mmol). Once the solution was homogeneous, 1-(3-dimethylaminopropyl)-3-ethylcarbodiimide hydrochloride (40 g, 200 mmol) was added. This mixture was allowed to stir at room temperature for 16 hrs and was then concentrated in vacuo. The residue was dissolved in ethyl acetate (500 mL) and this solution was washed twice with saturated aqueous ammonium chloride (400 mL), twice with saturated aqueous bicarbonate (400 mL), and twice with brine (400 mL). The organic solution was dried ($MgSO_4$), filtered and concentrated in vacuo to give 74.6 g (103%) of a straw colored syrup. This syrup was dissolved in p-dioxane (400 mL) and anhydrous HCl gas was bubbled through for 15 minutes and was allowed to stir for 3 hr at room temperature. The solution was concentrated in vacuo to give a yellow foam coating the sides of the flask. The foam was washed several times with diethyl ether and the solvent was decanted. The foam was dried under high vacuum to give 61 g (98%).

$^1$H NMR

FD-MS, m/e 353 (MH$^+$)

| Analysis for $C_{21}H_{25}N_2O_3Cl$ | | | |
|---|---|---|---|
| Calc: | C, 64.86; | H, 6.44; | N, 7.21 |
| Found: | C, 65.48; | H, 6.75; | N, 7.94. |

B) Preparation t-BuOOCCH$_2$-D-Phe-Pro-OBn.

To a solution of D-Phe-Pro-OBn.HCl (30 g, 77 mmol) in acetonitrile (400 mL) was added diisopropylethylamine (40 mL, 231 mmol) and t-butyl bromoacetate (13.7 mL, 85 mmol). This solution was brought to reflux and maintained there for 3 hrs. After cooling to room temp, the solution was concentrated in vacuo. The residue was dissolved in ethyl acetate (300 mL) and this solution was washed twice with saturated aqueous ammonium chloride (200 mL), twice with saturated aqueous sodium bicarbonate (200 mL), and twice with brine (200 mL). The organic layer was dried ($MgSO_4$), filtered, and concentrated in vacuo to give an orange oil which was purified by silica gel chromatography eluting with a gradient of hexanes to 1:1 hexanes/ethyl acetate. Fractions containing product (as judged by TLC) were combined and concentrated to give 23.6 g (66 %) of a colorless oil.

$^1$H NMR

FD-MS, m/e 466 (M$^+$)

C) Preparation of Boc-t-BuOOCCH$_2$-D-Phe-Pro-OBn.

To a solution of t-BuOOCCH$_2$-D-Phe-Pro-OBn (22.5 g, 48 mmol) in THF (200 mL) was added diisopropylethylamine (12.5 mL, 72 mmol) and di-t-butyl dicarbonate (11.6 g, 53 mmol). This solution was brought to gentle reflux and maintained for 16 hrs. Heating was discontinued, and once cool, the solution was concentrated in vacuo. The residue was dissolved in ethyl acetate (400 mL) and washed twice with 1.0M citric acid (200 mL), twice with saturated aqueous sodium bicarbonate (200 mL), and twice with brine (200 mL). The organic solution was dried ($MgSO_4$), filtered, and concentrated in vacuo to give a yellow oil which was purified by silica gel chromatography eluting with a gradient of hexanes to 2:1 hexanes/ethyl acetate. Fractions containing product(as judged by TLC) were combined and concentrated to give 23.7 g (87%) of a colorless oil.

$^1$H NMR

FD-MS, m/e 566 (M$^+$)

D) Preparation of Boc-t-BuOOCCH$_2$-D-Phe-Pro-OH.

To a solution of Boc-t-BuOOCCH$_2$-D-Phe-Pro-OBn (23 g, 41 mmol) in ethyl acetate (250 mL) was added 5% Pd/C catalyst (5 g). This solution was degassed in vacuo several times. A balloon filled with hydrogen was used to introduce the gas. The mixture was allowed to stir under a hydrogen atmosphere for 2 hrs with stirring. The balloon was removed, celite was added and the slurry was filtered over a pad of celite. The filtrate was concentrated in vacuo to give 18.7 g (96%) of a white foam.

$^1$H NMR

FD-MS, m/e 476 (M$^+$)

E) Preparation of HOOCCH$_2$-D-Phe-Pro-ArgH.HCl.

By methods substantially equivalent to those described in Example 1-H and 1-I, crude Boc-t-BuOOCCH$_2$-D-Phe-Pro-ArgH.HCl was prepared from Boc-t-BuOOCCH$_2$-D-Phe-Pro-OH. The crude residue was re-dissolved in 5% anisole/trifluoroacetic acid at 0° C. This was allowed to stir cold for 1 hour at which time the solvent was removed in vacuo. The residue was taken into 0.1N HCl and washed twice with diethyl ether. The aqueous layer was concentrated to a volume of 30 mL and the product was then purified by RPHPLC Method A to give 550 mg (22%) of pure HOOCCH$_2$-D-Phe-Pro-ArgH.HCl.

$^1$H NMR

FAB-MS, m/e 461.3 (MH$^+$)

| Analysis for $C_{22}H_{32}N_6O_5.1.5HCl$: | | | |
|---|---|---|---|
| Calc: | C, 51.29; | H, 6.55; | N, 16.31; |
| Found: | C, 51.40; | H, 6.42; | N, 16.15. |

EXAMPLE 36

Preparation of N-(carboxymethyl)-D-cyclohexylalanyl-L-Prolinyl-L-Arginine Aldehyde Hydrochloride

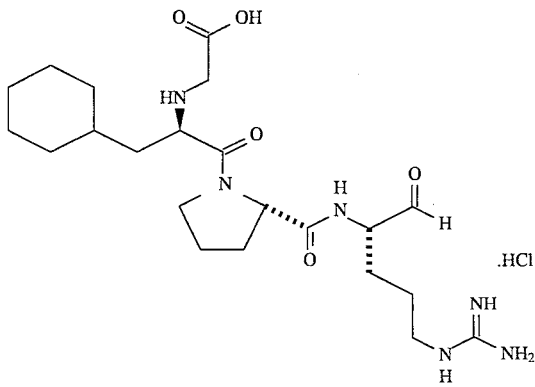

Preparation of $HOCCH_2$-D-Cha-Pro-ArgH.HCl.

By methods substantially equivalent to those described in example 35, 453 mg of $HOCCH_2$-D-Cha-Pro-ArgH.HCl were prepared from Boc-D-Cha.

$^1$H NMR

FAB-MS, m/e 467.3 ($MH^+$)

Analysis for $C_{22}H_{38}N_6O_5 \cdot 1.5HCl \cdot 0.5H_2O$:

| | | | |
|---|---|---|---|
| Calc: | C, 49.83; | H, 7.70; | N, 15.85; |
| Found: | C, 49.56; | H, 7.36; | N, 15.82. |

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment, an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic diseases such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other disorders (diseases) where blood coagulation could be a fundamental contributing process or a source of secondary pathology, such as cancer, including metastasis, inflammatory diseases, including arthritis, and diabetes. The anti-coagulant compound is administered orally or parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (tPA), modified tPA, streptokinase or urokinase. In cases when clot formation has occurred and an artery or vein is blocked, either partially or totally, a clot lysing agent is usually employed. A compound of the invention can be administered prior to or along with the lysing agent or subsequent to its use and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9%), 5% dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 ml sterile glass ampoule. Another example of a unit dosage formulation comprises about 10 mg of a compound of the present invention as a pharmaceutically acceptable salt in 20 ml of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcyrstalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcyrstalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl- pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active 15 ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The compounds provided by the invention (formula 1) selectively inhibit the action of thrombin in mammals.

The ability of the compounds of the present invention to be an effective thrombin inhibitor is evaluated in one or more of the following assays.

The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-Phe-Val-Arg-p-nitroanilide.

The assay is carried out by mixing 50 µl buffer (0.03M Tris, 0.15M NaCl, pH 7.4), 25 µl of human thrombin solution (purified human thrombin Enzyme Research Laboratories, South Bend, Ind.) at 8 NIH units/ml and 25 µl of test compound in a solvent (50% aqueous methanol (v:v)). Then 150 µl of an aqueous solution of the chromogenic substrate (at 0.25 mg/ml) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

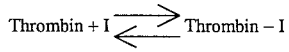

$$Kass = \frac{[\text{Thrombin I}]}{[(\text{Thrombin}) \times (I)]}$$

Kass is calculated for a range of concentrations of test compounds and the mean value is reported in units of liter per mole.

By substantially following the procedures described above for human thrombin, and using other human blood coagulation system serine proteases, and using fibrinolytic system serine proteases, with the appropriate chromogenic substrate, identified below, selectivity of the compounds of the present invention with respect to the coagulation factor serine proteases and to the fibrinolytic serine proteases are evaluated as well as their substantial lack of interference with human plasma clot fibrinolysis.

Human factors X, Xa, IXa, XIa, and xIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952 incorporated by reference herein in its entirety. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate) pyroglutamyl-Pro-Arg-p-nitroanilide (for factor XIa and for aPC); H-D-Pro-Phe-Arg-p-nitroanilide (for factor XIIa); and pyroglutamyl-Gly-Arg-p-nitroanilide (for urokinase); are purchased from KabiVitrum, Stockholm, Sweden, or from Midwest Biotech, Fishers, Indiana. Bovine trypsin is purchased from Worthington Biochemicals, Freehold, N.J., and human plasma kallikrein from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, known methods of peptide coupling from commercially available reactants, or was purchased from Midwest Biotech, Fishers, Ind. Human plasmin is purchased from Boehringer Mannheim, Indianapolis, Ind.; nt-PA is purchased as single chain activity reference from American Diagnostics, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminegen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass values obtained with the indicated compound represented by the formula 1.

TABLE 1

Serine Protease Inhibition

Enzyme Kass (L/mol × $10^6$)

| Example | Human Thrombin | Xa | Trypsin | Plasmin |
|---|---|---|---|---|
| 1 | 850. | 0.51 | 120. | 7.9 |
| 2 | 110. | 0.16 | 22. | 0.55 |
| 3 | 58. | 0.080 | 12. | 0.41 |
| 4 | 13. | 0.067 | 5.2 | 0.27 |
| 5 | 320. | 4.6 | 7.9 | 25. |
| 6 | 200. | 0.83 | 2.5 | 2.5 |
| 7 | 690. | 2.4 | 220. | 17. |
| 8 | 450. | 2.6 | 260. | 31. |
| 9 | 1,700. | 13. | 480. | 29. |
| 10 | 470. | 8.3 | 230. | 27. |
| 11 | 460. | 6.0 | 260. | 25. |
| 12 | 300. | 3.9 | 160. | 21. |
| 13 | 270. | 3.6 | 180. | 19. |
| 14 | 230. | 11. | 160. | 25. |
| 15 | 200. | 8.8 | 150. | 9.5 |
| 16 | 260. | 11. | 200. | 18. |
| 17 | N.T. | N.T. | N.T. | N.T. |
| 18 | 70. | 2.0 | 43. | 7.0 |
| 19 | 68. | 2.8 | 52. | 3.4 |
| 20 | 510. | 45. | 160. | 14. |
| 21 | 550. | 20. | 200. | 45. |
| 22 | 260. | 24. | 260. | 13. |
| 23 | 3.4 | 0.066 | 14. | 0.28 |
| 24 | 33. | 0.29 | 57. | 3.8 |
| 25 | 26. | 0.033 | 15. | 0.31 |
| 26 | 29. | 0.10 | 14. | 0.54 |
| 27 | 20. | 0.064 | 5.9 | 0.24 |
| 28 | 26. | 1.1 | 12. | 0.61 |
| 29 | 43. | 0.32 | 15. | 0.86 |
| 30 | 480. | 0.11 | 69. | 0.49 |
| 31 | 590. | 5.6 | 160. | 7.7 |
| 32 | 25. | 0.21 | 60. | 2.0 |
| 33 | 170. | 2.3 | 240. | 16. |
| 34 | 360. | 8.1 | 140. | 26. |
| 35 | 695. | 3.3 | | |
| 36 | 556. | 40.5 | | |

N.T. = Not Tested.

Thrombin inhibitors preferably should spare fibrinolysis induced by urokinase, tissue plasminogen activator (t-PA) and streptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostics, Greenwich, Conn. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Plough units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 ul thrombin (73 NIH unit/ml) to 100 ul human plasma which contained 0.0229 uCi 125-iodine labeled fibrinogen. Clot lysis is studied by overlaying the clots with 50 ul of urokinase or streptokinase (50, 100, or 1000 unit/ml) and incubating for 20 hours at room temperature. After incubation the tubes are centrifuged in a Beckman Microfuge. 25 ul of supernate is added into 1.0 ml volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/ml concentrations. Rough approximations of $IC_{50}$ values are estimated by linear extrapolations from data points to a value which would represent 50 percent of lysis for that particular concentration of fibrinolytic agent.

TABLE 2

Serine Protease Inhibition
Enzyme Kass (L/mol × $10^6$)

| Example No. | t-Pa |
|---|---|
| 1 | 31. |
| 2 | 0.32 |
| 3 | 0.17 |
| 4 | 0.22 |
| 5 | 1.1 |
| 6 | 0.088 |
| 7 | 13. |
| 8 | 2.9 |
| 9 | 2.8 |
| 10 | 0.83 |
| 11 | 3.5 |
| 12 | (100% inhib. at 13 μg/mL) |
| 13 | 2.3 |
| 14 | 2.4 |
| 15 | 1.5 |
| 16 | 2.7 |
| 17 | N.T. |
| 18 | 1.1 |
| 19 | 0.31 |
| 20 | 0.34 |
| 21 | 0.73 |
| 22 | 0.11 |
| 23 | 0.11 |

TABLE 2-continued

Serine Protease Inhibition
Enzyme Kass (L/mol × 10⁶)

| Example No. | t-Pa |
|---|---|
| 24 | 0.30 |
| 25 | 0.17 |
| 26 | 0.37 |
| 27 | 0.26 |
| 28 | 0.035 |
| 29 | 0.62 |
| 30 | 0.046 |
| 31 | 0.037 |
| 32 | 0.54 |
| 33 | 2.5 |
| 34 | 0.75 |

N.T. = Not Tested

Anticoagulant Activity

Materials

Dog plasma and rat plasma are obtained from conscious mixed-breed hounds (either sex, Hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. Chem. J.*, 185, 1–11 (1980); and Smith, et al., *Biochemistry*, 11, 2958–2967 (1972). Human fibrinogen is also purchased as 98 percent pure/plasmin free from American Diagnostics, Greenwich, Conn. Coagulation reagents ACTIN, Thromboplastin, and Human plasma are from Baxter Healthcare Corp., Dade Division, Miami, Fla. Bovine thrombin from Parke-Davis (Ann Arbor, Mich.) is used for coagulation assays in plasma.

Methods

Anticoagulation Determinations

Coagulation assay procedures are as previously described. Smith, et al., *Thrombosis Research*, 5, 163–174 (1988). A CoAScreener coagulation instrument (American LABor, Inc.) is used for all coagulation assay measurements. The prothrombin time (PT) is measured by adding 0.05 ml saline and 0.05 ml Thromboplastin-C reagent to 0.05 ml test plasma. The activated partial thromboplastin time (APTT) is measured by incubation of 0.05 ml test plasma with 0.05 ml Actin reagent for 120 seconds followed by 0.05 ml CaCl2 (0.02M). The thrombin time (TT) is measured by adding 0.05 ml saline and 0.05 ml thrombin (10 NIH units/ml) to 0.05 ml test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

TABLE 3

Anticoagulation Evaluations In Human Plasma

| | 2 × Clotting time (ng/ML) | | |
|---|---|---|---|
| Example No. | TT | APTT | PT |
| 1 | 43 | 440 | 870 |
| 2 | 35 | 1,100 | 1,400 |
| 3 | 47 | 1,300 | 1,700 |
| 4 | 150 | 2,300 | 3,400 |
| 5 | 110 | 1,000 | 2,500 |
| 6 | 97 | 1,400 | 2,700 |

TABLE 3-continued

Anticoagulation Evaluations In Human Plasma

| | 2 × Clotting time (ng/ML) | | |
|---|---|---|---|
| Example No. | TT | APTT | PT |
| 7 | 21 | 330 | 530 |
| 8 | 9 | 260 | 660 |
| 9 | 6 | 220 | 510 |
| 10 | 18 | 300 | 700 |
| 11 | 13 | 270 | 510 |
| 12 | 46 | 360 | 480 |
| 13 | 14 | 450 | 930 |
| 14 | 21 | 350 | 940 |
| 15 | 92 | 550 | 2,000 |
| 16 | 33 | 430 | 1,300 |
| 17 | N.T. | N.T. | N.T. |
| 18 | 120 | 1,200 | 3,000 |
| 19 | 66 | 810 | 2,900 |
| 20 | 34 | 250 | 880 |
| 21 | 25 | 260 | 730 |
| 22 | 46 | 330 | 1,100 |
| 23 | 140 | 2,700 | 4,100 |
| 24 | 38 | 440 | 1,200 |
| 25 | 59 | 1,300 | 1,800 |
| 26 | 64 | 1,100 | 2,000 |
| 27 | 63 | 1,300 | 1,800 |
| 28 | 92 | 1,900 | 3,500 |
| 29 | 150 | 3,500 | 4,800 |
| 30 | 16 | 860 | 1,200 |
| 31 | 18 | 420 | 720 |
| 32 | 63 | 1,100 | 1,700 |
| 33 | 22 | 390 | 2,000 |
| 34 | 48 | 410 | 890 |
| 35 | 14 | 723 | 1129 |
| 36 | 9 | 284 | 695 |

N.T. = Not Tested

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ model of arterial injury

The carotid arteries are isolated via a midline ventral cervical incision. A thermocouple is placed under each artery and vessel temperature is recorded continuously on a strip chart recorder. A cuff of tubing (0,058 ID×0.077 OD×4 mm, Baxter Med. Grade Silicone), cut longitudinally, is placed around each carotid directly above the thermocouple. $FeCl_3$ hexahydrate is dissolved in water and the concentration (20%) is expressed in terms of the actual weight of $FeCl_3$ only. To injure the artery and induce thrombosis, 2.85 ul is pipetted into the cuff to bathe the artery above the thermocouple probe. Arterial occlusion is indicated by a rapid drop in temperature. The time to occlusion is reported in minutes and represents the elapsed time between application of FeCl3 and the rapid drop in vessel temperature (see K. D. Kurz, *Thromb. Res.*, 60:269,1990).

Spontaneous thrombolysis model

In vitro data suggests that peptide thrombin inhibitors inhibit thrombin and at higher concentrations may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 ml) is mixed rapidly with bovine thrombin (4 IU, Parke Davis) and $^{125}$I human fibrogen (5 µCi, ICN), immediately drawn into silastic tubing and incubated at 37° C. for 1 hr. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.*, 12:520, 1988).

Coagulation parameters

Plasma thrombin time (TT) and activated partial thromboplastin time (APTT) are measured with a fibrometer. Blood is sampled from a jugular catheter and collected in syringe containing sodium citrate (3.8%, 1 part to 9 parts blood). To measure TT, rat plasma (0.1 ml) is mixed with saline (0.1 ml) and bovine thrombin (0.1 ml, 30 U/ml in TRIS buffer; Parke Davis) at 37° C. For APTT, plasma (0.1 ml) and APTT solution (0.1 ml, Organon Teknika are incubated for 5 minutes (37° C.) and CaCl$_2$ (0.01 ml, 0,025M) is added to start coagulation. Assays are done in duplicate and averaged.

Index of Bioavailability

A measure of bioactivity, plasma thrombin time (TT), serves as a substitute for the assay of parent compound on the assumption that increments in TT result from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{\text{AUC po}}{\text{AUC iv}} \times \frac{\text{Dose iv}}{\text{Dose po}} \times 100$$

Compounds

Compound solutions are prepared fresh daily in normal saline and are injected as a bolus or are infused starting 15 min before and continuing throughout the experimental perturbation which is 15 minutes in the arteriovenous shunt model and 60 minutes in the FeCl$_3$ model of arterial injury and in the spontaneous thrombolysis model. Bolus injection volume is 1 ml/kg for i.v., and 5 ml/kg for p.o. and infusion volume is 3 ml/hr.

Statistics

Results are expressed as means ± SEM. One-way analysis of variance is used to detect statistically significant differences and then Dunnett's test is applied to determine which means are different. Significance level for rejection of the null hypothesis of equal means is P<0.05.

TABLE 4

Index of Bioavailability

| Example | % Relative Activity |
|---------|---------------------|
| 1 | 2 |
| 2 | 1 |
| 3 | 3 |
| 4 | N.T.[a] |
| 5 | N.T. |
| 6 | N.T. |
| 7 | 27 |
| 8 | 31 |
| 9 | 14 |
| 10 | 18 |
| 11 | 10 |
| 12 | 26 |
| 13 | 3 |
| 14 | 6 |
| 15 | N.T. |
| 16 | N.T. |
| 17 | N.T. |
| 18 | 13 |
| 19 | N.T. |
| 20 | N.T. |
| 21 | 19 |
| 22 | N.T. |
| 23 | N.T. |
| 24 | N.T. |
| 25 | N.T. |
| 26 | N.T. |
| 27 | N.T. |
| 28 | 9 |
| 29 | N.T. |
| 30 | 1 |
| 31 | 13 |
| 32 | N.T. |
| 33 | 14 |
| 34 | N.T. |

N.T. = Not Tested.

Animals

Male dogs (Beagles; 18 months—2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50% relative humidity; and lighted from 0600–1800 hours.

Pharmacokinetic model.

Test compound is formulated immediately prior to dosing by dissolving in sterile 0.9% saline to a 5 mg/ml preparation. Dogs are given a single 2 mg/kg dose of test compound by oral gavage. Blood samples (4.5 ml) are taken from the cephalic vein at 0.25, 0.5, 0.75, 1,2,3,4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to pH7 with phosphoric acid (60:40, v/v). Plasma concentration of test compound is recorded and used to calculate the pharmacokinetic parameters: elimination rate constant, Ke;

total clearance, Clt; volume of distribution, $V_D$; time of maximum plasma test compound concentration, Tmax; maximum concentration of test compound at Tmax, Cmax; plasma half-life, t0.5; area under the curve, A.U.C.; and fraction of test compound absorbed, F.

Model of Coronary artery Thrombosis

Surgical preparation and instrumentation of the dogs are as described in Jackson, et al., *Circulation*, 82, 930–940 (1990). Mixed-breed hounds (aged 6–7 months, either sex, Hazelton-LRE, Kalamazoo, Mich. U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50% inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100 µA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 h. A 2-h infusion of the compounds of the present invention at doses of 0.5 and 1 mg/kg/h is begun simultaneously with an infusion of thrombotic agent (e.g. tissue plasminogen activator, streptokinase, APSAC). Reperfusion is followed for 3 h after administration of test compound. Reocclusion of coronary arteries after successful thrombolysis is defined as zero CBF which persisted for $\geq 30$ min.

Hematology and template bleeding time determinations

Whole blood cell counts, hemoglobin, and hematocrit values are determined on a 40-µl sample of citrated (3.8%) blood (1 part citrate:9 parts blood) with a hematology analyzer (Cell-Dyn 900, Sequoia-Turner. Mount View, Calif. U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean ±SEM. All studies are conducted in accordance with the guiding principles of the American Physiological Society. Further details regarding the procedures are described in Jackson, et al., *J. Cardiovasc. Pharmacol.*, 21, 587–599 (1993).

We claim:

1. A compound having the $$Y-\overset{O}{\overset{\|}{C}}-X-\overset{H}{\underset{}{N}}-\overset{*}{\underset{\underset{R^1}{\overset{|}{C=O}}}{CH}}-(CH_2)_3-\overset{H}{\underset{}{N}}-\overset{NH}{\overset{\|}{C}}-NH_2 \quad I$$

where $R^1$ is hydrogen;

X is prolinyl or azetidinyl-2-carbonyl;

Y is a group

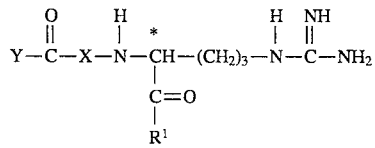

where R is benzyl, phenyl, cyclopentyl, cyclohexyl, cyclopentyl-$CH_2$— or cyclohexyl-$CH_2$—;

Z is

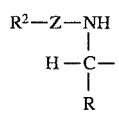

—S(O)n— or a bond;

$R^2$ is $C_1$–$C_6$ alkyl, $C_1$–$C_2$ perfluoroalkyl, —$(CH_2)_g$—COOH, $C_1$–$C_6$ alkoxy, ($C_1$–$C_4$ alkoxy)$C_1$–$C_4$ alkyl, cyclopentyl, cyclohexyl, ($C_5$–$C_6$ cycloalkyl)$CH_2$—, amino, mono ($C_1$–$C_4$)alkylamino, di($C_1$–$C_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

g is 1, 2 or 3;

n is 1 or 2; and pharmaceutically acceptable salts and solvates thereof;

provided that when R is benzyl, phenyl, cyclopentyl or cyclohexyl and Z is

or a bond, $R^2$ is other than $C_1$–$C_6$alkyl, $C_1$–$C_2$ perfluoroalkyl, $C_1$–$C_6$ alkoxy or unsubstituted phenyl; and further provided that when Z is —S(O)n—, then $R^2$ is other than unsubstituted or substituted naphthyl or a 9 or 10 membered unsubstituted or substituted fused bicyclic heterocyclic ring.

2. A compound of claim 1 where
$R^1$ is hydrogen;
X is prolinyl or azetidinyl-2-carbonyl;
Y is a group

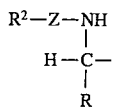

where R is benzyl, phenyl, cyclopentyl, cyclohexyl, cyclopentyl-$CH_2$— or cyclohexyl-$CH_2$—;
Z is

—S(O)n— or a bond;

$R^2$ is $C_1$–$C_6$ alkyl, $C_1$–$C_2$ perfluoroalkyl, $C_1$–$C_6$ alkoxy, ($C_1$–$C_4$ alkoxy)$C_1$–$C_4$ alkyl, cyclopentyl, cyclohexyl, ($C_5$–$C_6$ cycloalkyl)$CH_2$—, amino, mono($C_1$–$C_4$)alkylamino, di($C_1C_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

n is 1 or 2; and pharmaceutically acceptable salts and solvates thereof;

provided that when R is benzyl, phenyl, cyclopentyl or cyclohexyl and Z is

or a bond, $R^2$ is other than $C_1$–$C_6$ alkyl, $C_1$–$C_2$ perfluoroalkyl, $C_1$–$C_6$ alkoxy or unsubstituted phenyl; and further provided that when Z is —S(O)n—, then $R^2$ is other than unsubstituted or substituted naphthyl or a 9 or 10 membered unsubstituted or substituted fused bicyclic heterocyclic ring.

3. A compound of claim 2 where
$R^1$ is hydrogen;

$R^2$ is $C_1$–$C_6$ alkyl, amino, mono($C_1$–$C_4$ alkyl)amino, di($C_1$–$C_4$ alkyl)amino, or a 9 or 10 membered unsubstituted or monosubstituted fused bicyclic heterocyclic ring; and pharmaceutically acceptable salts and solvates thereof;

provided that when R is benzyl, phenyl, cyclopentyl or cyclohexyl and Z is

or a bond, $R^2$ is other than $C_1$–$C_6$ alkyl; and further provided that when Z is —S(O)n—, then $R^2$ is other than unsubstituted or substituted naphthyl or a 9 or 10 membered unsubstituted or substituted fused bicyclic heterocyclic ring.

4. A compound of claim 3 where
$R^1$ is hydrogen;
R is benzyl or cyclohexyl-$CH_2$—;
Z is

$R^2$ is a 9 or 10 membered unsubstituted or monosubstituted fused bicyclic heterocyclic ring containing one nitrogen atom and where the substituent is selected from $C_1$–$C_4$ alkyl, amino, mono($C_1$–$C_4$ alkyl)amino, di($C_1$–$C_4$ alkyl)amino, and —$NHSO_2$($C_1$–$C_4$ alkyl);

and pharmaceutically acceptable salts and solvates thereof.

5. A compound of claim 3 where
$R^1$ is hydrogen;
Z is —$SO_2$—;
$R^2$ is $C_1$–$C_6$ alkyl, amino, mono($C_1$–$C_4$ alkyl)amino or di ($C_1$–$C_4$ alkyl) amino; and pharmaceutically acceptable salts and solvates thereof.

6. A compound of claim 1 where
$R^1$ is hydrogen;
X is prolinyl or azetidinyl-2-carbonyl;
z is a bond;
$R^2$ is —$(CH_2)_g$—COOH;
g is 1, 2 or 3; and pharmaceutically acceptable salts and solvates thereof.

7. A compound of claim 4 which is N-(1-methylindolyl-2-carbonyl)-D-phenylalanyl-L-prolinyl-L-arginine aldehyde and pharmaceutically acceptable salts and solvates thereof.

8. A compound of claim 4 which is N-(quinolinyl-2-carbonyl)-D-phenylalanyl-L-prolinyl-L-arginine aldehyde and pharmaceutically acceptable salts and solvates thereof.

9. A compound of claim 4 which is N-(1-methylindolyl-2-carbonyl)-D-cyclohexylalanyl-L-prolinyl-L-arginine aldehyde and pharmaceutically acceptable salts and solvates thereof.

10. A compound of claim 4 which is N-(quinolinyl-2-carbonyl)-D-cyclohexylalanyl-L-prolinyl-L-arginine aldehyde and pharmaceutically acceptable salts and solvates thereof.

11. A compound of claim 5 which is N-(methylsulfonyl)-D-phenylalanyl-L-prolinyl-L-arginine aldehyde and pharmaceutically acceptable salts and solvates thereof.

12. A compound of claim 5 which is N-(ethylsulfonyl)-D-phenylalanyl-L-prolinyl-L-arginine aldehyde and pharmaceutically acceptable salts and solvates thereof.

13. A compound of claim 5 which ms N-(n-propylsulfonyl)-D-phenylalanyl-L-prolinyl-L-arginine aldehyde and pharmaceutically acceptable salts and solvates thereof.

14. A compound of claim 5 which ms N-(dimethylaminosulfonyl)-D-phenylalanyl-L-prolinyl-L-arginine aldehyde and pharmaceutically acceptable salts and solvates thereof.

15. A compound of claim 5 which is N-(ethylsulfonyl)-D-phenylglycinyl-L-prolinyl-L-arginine aldehyde and pharmaceutically acceptable salts and solvates thereof.

16. A compound of claim 5 which is N-(ethylsulfonyl)-D-cyclohexylalanyl-L-prolinyl-L-arginine aldehyde and pharmaceutically acceptable salts and solvates thereof.

17. A compound of claim 5 which ms N-(ethylsulfonyl)-D-cyclohexylglycinyl-L-prolinyl-L-arginine aldehyde and pharmaceutically acceptable salts and solvates thereof.

18. A compound of claim 6 which ms N-(carboxymethyl)-D-cyclohexylalanyl-L-prolinyl-L-arginine aldehyde and pharmaceutically acceptable salts and solvates thereof.

19. A pharmaceutical formulation comprising in association with a pharmaceutically acceptable carrier, diluent, or excipient, a compound of the formula

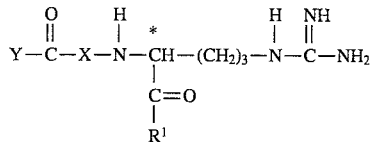   I where $R^1$ is hydrogen;

X is prolinyl or azetidinyl-2-carbonyl;

Y is a group

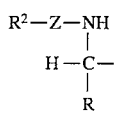

where R is benzyl, phenyl, cyclopentyl, cyclohexyl, cyclopentyl-$CH_2$— or cyclohexyl-$CH_2$—;

Z is

—S(O)n— or a bond;

$R^2$ is $C_1$–$C_6$ alkyl, $C_1$–$C_2$ perfluoroalkyl, —$(CH_2)_g$—COOH, $C_1$–$C_6$ alkoxy, ($C_1$–$C_4$ alkoxy)$C_1$–$C_4$ alkyl, cyclopentyl, cyclohexyl, ($C_5$–$C_6$ cycloalkyl)$CH_2$—, amino, mono ($C_1$–$C_4$)alkylamino, di($C_1$–$C_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

g is 1, 2 or 3;

n is 1 or 2; and pharmaceutically acceptable salts and solvates thereof;

provided that when R is benzyl, phenyl, cyclopentyl or cyclohexyl and Z is

or a bond, $R^2$ is other than $C_1$–$C_6$ alkyl, $C_1$–$C_2$ perfluoroalkyl, $C_1$–$C_6$ alkoxy or unsubstituted phenyl; and further provided that when Z is —S(O)n—, then $R^2$ is other than unsubstituted or substituted naphthyl or a 9 or 10 membered unsubstituted or substituted fused bicyclic heterocyclic ring.

20. A formulation of claim 19 where $R^1$ is hydrogen;

X is prolinyl or azetidinyl-2-carbonyl;

Y is a group

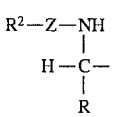

where R is benzyl, phenyl, cyclopentyl, cyclohexyl, cyclopentyl-$CH_2$— or cyclohexyl-$CH_2$—;

Z is

—S(O)n— or a bond;

$R^2$ is $C_1$–$C_6$ alkyl, $C_1$–$C_2$ perfluoroalkyl, $C_1$–$C_6$ alkoxy, ($C_1$–$C_4$ alkoxy)$C_1$–$C_4$ alkyl, cyclopentyl, cyclohexyl, ($C_5$–$C_6$ cycloalkyl)$CH_2$—, amino, mono ($C_1$–$C_4$)alkylamino, di($C_1$–$C_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

n is 1 or 2; and pharmaceutically acceptable salts and solvates thereof;

provided that when R is benzyl, phenyl, cyclopentyl or cyclohexyl and Z is

or a bond, $R^2$ is other than $C_1$–$C_6$ alkyl, $C_1$–$C_2$ perfluoroalkyl, $C_1$–$C_6$ alkoxy or unsubstituted phenyl; and further provided that when Z is —S(O)n—, then $R^2$ is other than unsubstituted or substituted naphthyl or a 9 or 10 membered unsubstituted or substituted fused bicyclic heterocyclic ring.

21. A formulation of claim 20 where $R^1$ is hydrogen;

$R^2$ is $C_1$–$C_6$ alkyl, amino, mono($C_1$–$C_4$ alkyl)amino, di($C_1$–$C_4$ alkyl)amino, or a 9 or 10 membered unsubstituted or monosubstituted fused bicyclic heterocyclic ring; and pharmaceutically acceptable salts and solvates thereof;

provided that when R is benzyl, phenyl, cyclopentyl or cyclohexyl and Z is

or a bond, $R^2$ is other than $C_1$-$C_6$ alkyl; and further provided that when Z is —S(O)n—, then $R_2$ is other than unsubstituted or substituted naphthyl or a 9 or 10 membered unsubstituted or substituted fused bicyclic heterocyclic ring.

22. A formulation of claim 21 where
$R^1$ is hydrogen;
R is benzyl or cyclohexyl-$CH_2$—;
Z is

$R^2$ is a 9 or 10 membered unsubstituted or monosubstituted fused bicyclic heterocyclic ring containing one nitrogen atom and where the substituent is selected from $C_1$-$C_4$ alkyl, amino, mono($C_1$-$C_4$ alkyl)amino, di($C_1$-$C_4$ alkyl)amino, and —$NHSO_2(C_1$ -$C_4$ alkyl);
and pharmaceutically acceptable salts and solvates thereof.

23. A formulation of claim 21 where
$R^1$ is hydrogen;
Z is —$S_2$—;
$R^2$ is $C_1$-$C_6$ alkyl, amino, mono $C_1$-$C_4$ alkyl)amino or di($C_1$-$C_4$ alkyl) amino;
and pharmaceutically acceptable salts and solvates thereof.

24. A formulation of claim 19 where
$R^1$ is hydrogen;
X is prolinyl or azetidinyl-2-carbonyl;
Z is a bond;
$R^2$ is —$(CH_2)_g$—COOH;
g is 1, 2 or 3; and pharmaceutically acceptable salts and solvates thereof.

25. A formulation of claim 22 where said compound is N-(1-methylindolyl-2-carbonyl)-D-phenylalanyl-L-prolinyl-L-arginine aldehyde and pharmaceutically acceptable salts and solvates thereof.

26. A formulation of claim 22 where said compound is N-(quinolinyl-2-carbonyl)-D-phenylalanyl-L-prolinyl-L-arginine aldehyde and pharmaceutically acceptable salts and solvates thereof.

27. A formulation of claim 22 where said compound is N-(1-methylindolyl-2-carbonyl)-D-cyclohexylalanyl-L-prolinyl-L-arginine aldehyde and pharmaceutically acceptable salts and solvates thereof.

28. A formulation of claim 22 where said compound is N-(quinolinyl-2-carbonyl)-D-cyclohexylalanyl-L-arginine aldehyde and pharmaceutically acceptable salts and solvates thereof.

29. A formulation of claim 23 where said compound is N-(methylsulfonyl)-D-phenylalanyl-L-prolinyl-L-arginine aldehyde and pharmaceutically acceptable salts and solvates thereof.

30. A formulation of claim 23 where said compound is N-(ethylsulfonyl)-D-phenylalanyl-L-prolinyl-L-arginine aldehyde and pharmaceutically acceptable salts and solvates thereof.

31. A formulation of claim 23 where said compound is N-(n-propylsulfonyl)-D-phenylalanyl-L-prolinyl-L-arginine aldehyde and pharmaceutically acceptable salts and solvates thereof.

32. A formulation of claim 23 where said compound is N-(dimethylaminosulfonyl)-D-phenylalanyl-L-prolinyl-L-arginine aldehyde and pharmaceutically acceptable salts and solvates thereof.

33. A formulation of claim 23 where said compound is N-(ethylsulfonyl)-D-phenylglycinyl-L-prolinyl-L-arginine aldehyde and pharmaceutically acceptable salts and solvates thereof.

34. A formulation of claim 23 where said compound is N-(ethylsulfonyl)-D-cyclohexylalanyl-L-prolinyl-L-arginine aldehyde and pharmaceutically acceptable salts and solvates thereof.

35. A formulation of claim 23 where said compound is N-(ethylsulfonyl)-D-cyclohexylglycinyl-L-prolinyl-L-arginine aldehyde and pharmaceutically acceptable salts and solvates thereof.

36. A formulation of claim 24 where said compound is N-(carboxymethyl)-D-cyclohexylalanyl-L-prolinyl-L-arginine aldehyde and pharmaceutically acceptable salts and solvates thereof.

37. A method of inhibiting thrombin in mammals, comprising administering to a mammal requiring thrombin inhibition, an effective dose of a compound having the formula

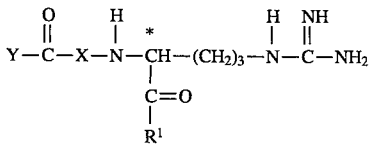

where
$R^1$ is hydrogen;
X is prolinyl or azetidinyl-2-carbonyl;
Y is a group

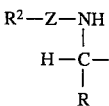

where R is benzyl, phenyl, cyclopentyl, cyclohexyl, cyclopentyl-$CH_2$— or cyclohexyl-$CH_2$—;
Z is

—S(O)n— or a bond;
$R^2$ is $C_1$-$C_6$ alkyl, $C_1$-$C_2$ perfluoroalkyl, —$(CH_2)_g$—COOH, $C_1$-$C_6$ alkoxy, ($C_1$-$C_4$ alkoxy)$C_1$-$C_4$ alkyl, cyclopentyl, cyclohexyl, ($C_5$-$C_6$ cycloalkyl)$CH_2$—, amino, mono ($C_1$-$C_4$)alkylamino, di($C_1$-$C_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

g is 1, 2 or 3;

n is 1 or 2; and pharmaceutically acceptable salts and solvates thereof;

provided that when R is benzyl, phenyl, cyclopentyl or cyclohexyl and Z is

or a bond, $R^2$ is other than $C_1$–$C_6$ alkyl, $C_1$–$C_2$ perfluoroalkyl, $C_1$–$C_6$ alkoxy or unsubstituted phenyl; and further provided that when Z is —S(O)n—, then $R^2$ is other than unsubstituted or substituted naphthyl or a 9 or 10 membered unsubstituted or substituted fused bicyclic heterocyclic ring.

38. The method of claim 37 where $R^1$ is hydrogen;

X is prolinyl or azetidinyl-2-carbonyl;

Y is a group

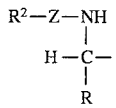

where R is benzyl, phenyl, cyclopentyl, cyclohexyl, cyclopentyl-CH$_2$— or cyclohexyl-CH$_2$—;

Z is

—S(O)n— or a bond;

$R^2$ is $C_1$–$C_6$ alkyl, $C_1$–$C_2$ perfluoroalkyl, $C_1$–$C_6$ alkoxy, ($C_1$–$C_4$ alkoxy)$C_1$–$C_4$ alkyl, cyclopentyl, cyclohexyl, ($C_5$–$C_6$ cycloalkyl)CH$_2$—, amino, mono($C_1$–$C_4$)alkylamino, di($C_1$C$_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

n is 1 or 2; and pharmaceutically acceptable salts and solvates thereof;

provided that when R is benzyl, phenyl, cyclopentyl or cyclohexyl and Z is

or a bond, $R^2$ is other than $C_1$–$C_6$ alkyl $C_1$–$C_2$ perfluoroalkyl, $C_1$–$C_6$ alkoxy or unsubstituted phenyl; and further provided that when Z is —S(O)n—, then $R^2$ is other than unsubstituted or substituted naphthyl or a 9 or 10 membered unsubstituted or substituted fused bicyclic heterocyclic ring.

39. The method of claim 38 where $R^1$ is hydrogen;

$R^2$ is $C_1$–$C_6$ alkyl, amino, mono($C_1$–$C_4$ alkyl)amino, di($C_1$–$C_4$ alkyl)amino, or a 9 or 10 membered unsubstituted or monosubstituted fused bicyclic heterocyclic ring; and pharmaceutically acceptable salts and solvates thereof;

provided that when R is benzyl, phenyl, cyclopentyl or cyclohexyl and Z is

or a bond, $R^2$ is other than $C_1$–$C_6$ alkyl; and further provided that when Z is —S(O)n—, then $R^2$ is other than unsubstituted or substituted naphthyl or a 9 or 10 membered unsubstituted or substituted fused bicyclic heterocyclic ring.

40. The method of claim 34 where $R^1$ is hydrogen;

R is benzyl or cyclohexyl-CH$_2$—;

Z is

$R^2$ is a 9 or 10 membered unsubstituted or monosubstituted fused bicyclic heterocyclic ring containing one nitrogen atom and where the substituent is selected from $C_1$–$C_4$ alkyl, amino, mono($C_1$–$C_4$ alkyl)amino, di($C_1$–$C_4$ alkyl)amino, and —NHSO$_2$($C_1$–$C_4$ alkyl);

and pharmaceutically acceptable salts and solvates thereof.

41. The method of claim 39 where $R^1$ is hydrogen;

Z is —SO$_2$—;

$R^2$ is $C_1$–$C_6$ alkyl, amino, mono($C_1$–$C_4$ alkyl)amino or di($C_1$–$C_4$ alkyl)amino;

and pharmaceutically acceptable salts and solvates thereof.

42. A compound of claim 37 where $R^1$ is hydrogen;

X is prolinyl or azetidinyl-2-carbonyl;

z is a bond;

$R^2$ is —(CH$_2$)$_g$—COOH;

g is 1, 2 or 3; and pharmaceutically acceptable salts and solvates thereof.

43. The method of claim 40 where said compound is N-(1-methylindolyl-2-carbonyl)-D-phenylalanyl-L-prolinyl-L-arginine aldehyde and pharmaceutically acceptable salts and solvates thereof.

44. The method of claim 40 where said compound is N-(quinolinyl-2-carbonyl)-D-phenylalanyl-L-prolinyl-L-arginine aldehyde and pharmaceutically acceptable salts and solvates thereof.

45. The method of claim 40 where said compound is N-(1-methylindolyl-2-carbonyl)-D-cyclohexylalanyl-L-prolinyl-L-arginine aldehyde and pharmaceutically acceptable salts and solvates thereof.

46. The method of claim 40 where said compound is N-(quinolinyl-2-carbonyl)-D-cyclohexylalanyl-L-prolinyl-L-arginine aldehyde and pharmaceutically acceptable salts and solvates thereof.

47. The method of claim 41 where said compound is N-(methylsulfonyl)-D-phenylalanyl-L-prolinyl-L-arginine aldehyde and pharmaceutically acceptable salts and solvates thereof.

48. The method of claim 41 where said compound is N-(ethylsulfonyl)-D-phenylalanyl-L-prolinyl-L-arginine aldehyde and pharmaceutically acceptable salts and solvates thereof.

49. The method of claim 41 where said compound is N-(n-propylsulfonyl)-D-phenylalanyl-L-prolinyl-L-arginine aldehyde and pharmaceutically acceptable salts and solvates thereof.

50. The method of claim 41 where said compound is N-(dimethylaminosulfonyl)-D-phenylalanyl-L-prolinyl-L-arginine aldehyde and pharmaceutically acceptable salts and solvates thereof.

51. The method of claim 41 where said compound is N-(ethylsulfonyl)-D-phenylglycinyl-L-prolinyl-L-arginine aldehyde and pharmaceutically acceptable salts and solvates thereof.

52. The method of claim 41 where said compound is N-(ethylsulfonyl)-D-cyclohexylalanyl-L-prolinyl-L-arginine aldehyde and pharmaceutically acceptable salts and solvates thereof.

53. The method of claim 41 where said compound is N-(ethylsulfonyl)-D-cyclohexylglycinyl-L-prolinyl-L-arginine aldehyde and pharmaceutically acceptable salts and solvates thereof.

54. The method of claim 42 where said compound is N-(carboxymethyl)-D-cyclohexylalanyl-L-prolinyl-L-arginine aldehyde and pharmaceutically acceptable salts and solvates thereof.

55. A method of inhibiting coagulation in mammals comprising administering to a mammal requiring coagulation inhibition, an effective dose of a compound having the formula

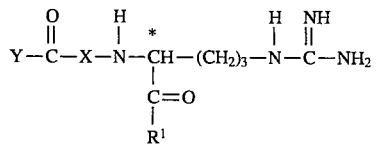

where $R^1$ is hydrogen;

X is prolinyl or azetidinyl-2-carbonyl;

Y is a group

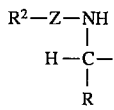

where R is benzyl, phenyl, cyclopentyl, cyclohexyl, cyclopentyl-$CH_2$— or cyclohexyl-$CH_2$—;

Z is

—S(O)n— or a bond;

$R^2$ is $C_1$–$C_6$ alkyl, $C_1$–$C_2$ perfluoroalkyl, —$(CH_2)_g$—COOH, $C_1$–$C_6$ alkoxy, ($C_1$–$C_4$ alkoxy)$C_1$–$C_4$ alkyl, cyclopentyl, cyclohexyl, ($C_5$–$C_6$ cycloalkyl)$CH_2$—, amino, mono ($C_1C_4$)alkylamino, di($C_1$–$C_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

g is 1, 2 or 3;

n is 1 or 2; and pharmaceutically acceptable salts and solvates thereof;

provided that when R is benzyl, phenyl, cyclopentyl or cyclohexyl and Z is

or a bond, $R^2$ is other than $C_1$–$C_6$ alkyl, $C_1$–$C_2$ perfluoroalkyl, $C_1$–$C_6$ alkoxy or unsubstituted phenyl; and further provided that when Z is —S(O)n—, then $R^2$ is other than unsubstituted or substituted naphthyl or a 9 or 10 membered unsubstituted or substituted fused bicyclic heterocyclic ring.

56. The method of claim 55 where $R^1$ is hydrogen;

X is prolinyl or azetidinyl-2-carbonyl;

Y is a group

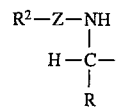

where R is benzyl, phenyl, cyclopentyl, cyclohexyl, cyclopentyl-$CH_2$— or cyclohexyl-$CH_2$—;

Z is

—S(O)n— or a bond;

$R^2$ is $C_1$–$C_6$ alkyl, $C_1$–$C_2$ perfluoroalkyl, $C_1$–$C_6$ alkoxy, ($C_1$–$C_4$ alkoxy)$C_1$–$C_4$ alkyl, cyclopentyl, cyclohexyl, ($C_5$–$C_6$ cycloalkyl)$CH_2$—, amino, mono ($C_1C_4$)alkylamino, di($C_1C_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

n is 1 or 2; and pharmaceutically acceptable salts and solvates thereof;

provided that when R is benzyl, phenyl, cyclopentyl or cyclohexyl and Z is $$\overset{O}{\underset{\|}{-C-}}$$

or a bond, $R^2$ is other than $C_1$–$C_6$ alkyl, $C_1$–$C_2$ perfluoroalkyl or $C_1$–$C_6$ alkoxy or unsubstituted phenyl; and further provided that when Z is —S(O)n—, then $R^2$ is other than unsubstituted or substituted naphthyl or a 9 or 10 membered unsubstituted or substituted fused bicyclic heterocyclic ring.

57. The method of claim 56 where $R^1$ is hydrogen;

$R^2$ is $C_1$–$C_6$ alkyl, amino, mono($C_1$–$C_4$ alkyl)amino, di($C_1$–$C_4$ alkyl)amino, or a 9 or 10 membered unsubstituted or monosubstituted fused bicyclic heterocyclic ring; and pharmaceutically acceptable salts and solvates thereof; provided that when R is benzyl, phenyl, cyclopentyl or cyclohexyl and Z is $$\overset{O}{\underset{\|}{-C-}}$$

or a bond, $R^2$ is other than $C_1$–$C_6$ alkyl, and further provided that when Z is —S(O)n—, then $R^2$ is other than unsubstituted o substituted naphthyl or a 9 or 10 membered unsubstituted or substituted fused bicyclic heterocyclic ring.

58. The method of claim 57 where $R^1$ is hydrogen;

R is benzyl or cyclohexyl-$CH_2$—;

Z is $$\overset{O}{\underset{\|}{-C-}};$$

$R^2$ is a 9 or 10 membered unsubstituted or monosubstituted fused bicyclic heterocyclic ring containing one nitrogen atom and where the substituent is selected from $C_1$–$C_4$alkyl, amino, mono($C_1$–$C_4$ alkyl)amino, di($C_1$–$C_4$ alkyl)amino, and —$NHSO_2$($C_1$–$C_4$ alkyl);

and pharmaceutically acceptable salts and solvates thereof.

59. The method of claim 57 where $R^1$ is hydrogen;

Z is —$SO_2$—;

$R^2$ is $C_1$–$C_6$ alkyl, amino, mono($C_1$–$C_4$ alkyl)amino or di($C_1$–$C_4$ alkyl)amino;

and pharmaceutically acceptable salts and solvates thereof.

60. The method of claim 55 where $R^1$ is hydrogen;

X is prolinyl or azetidinyl-2-carbonyl;

Z is a bond;

R is—$(CH_2)_g$—COOH;

g is 1, 2 or 3; and pharmaceutically acceptable salts and solvates thereof.

61. The method of claim 58 where said compound is N-(1-methylindolyl-2-carbonyl)-D-phenylalanyl-L-prolinyl-L-arginine aldehyde and pharmaceutically acceptable salts and solvates thereof.

62. The method of claim 58 where said compound is N-(quinolinyl-2-carbonyl)-D-phenylalanyl-L-prolinyl-L-arginine aldehyde and pharmaceutically acceptable salts and solvates thereof.

63. The method of claim 58 where said compound is N-(1-methylindolyl-2-carbonyl)-D-cyclohexylalanyl-L-prolinyl-L-arginine aldehyde and pharmaceutically acceptable salts and solvates thereof.

64. The method of claim 58 where said compound is N-(quinolinyl-2-carbonyl)-D-cyclohexylalanyl-L-prolinyl-L-arginine aldehyde and pharmaceutically acceptable salts and solvates thereof.

65. The method of claim 59 where said compound is N-(methylsulfonyl)-D-phenylalanyl-L-prolinyl-L-arginine aldehyde and pharmaceutically acceptable salts and solvates thereof.

66. The method of claim 59 where said compound is N-(ethylsulfonyl)-D-phenylalanyl-L-prolinyl-L-arginine aldehyde and pharmaceutically acceptable salts and solvates thereof.

67. The method of claim 59 where said compound is N-(n-Propylsulfonyl)-D-phenylalanyl-L-prolinyl-L-arginine aldehyde and pharmaceutically acceptable salts and solvates thereof.

68. The method of claim 59 where said compound is N-(dimethylaminosulfonyl)-D-phenylalanyl-L-prolinyl-L-arginine aldehyde and pharmaceutically acceptable salts and solvates thereof.

69. The method of claim 59 where said compound is N-(ethylsulfonyl)-D-phenylglycinyl-L-prolinyl-L-arginine aldehyde and pharmaceutically acceptable salts and solvates thereof.

70. The method of claim 59 where said compound is N-(ethylsulfonyl)-D-cyclohexylalanyl-L-prolinyl-L-arginine aldehyde and pharmaceutically acceptable salts and solvates thereof.

71. The method of claim 59 where said compound is N-(ethylsulfonyl)-D-cyclohexylglycinyl-L-prolinyl-L-arginine aldehyde and pharmaceutically acceptable salts and solvates thereof.

72. The method of claim 60 where said compound is N-(carboxymethyl)-D-cyclohexylalanyl-L-prolinyl-L-arginine aldehyde and pharmaceutically acceptable salts thereof.

73. A method of treating a thromboembolic disorder in mammals comprising administering to a mammal requiring treatment an effective dose of a compound having the formula $$Y-\overset{O}{\underset{\|}{C}}-X-\overset{H}{\underset{|}{N}}-\overset{*}{\underset{\underset{R^1}{\overset{|}{C=O}}}{CH}}-(CH_2)_3-\overset{H}{\underset{|}{N}}-\overset{NH}{\underset{\|}{C}}-NH_2 \qquad I$$

where $R^1$ is hydrogen;

X is prolinyl or azetidinyl-2-carbonyl;

Y is a group $$\underset{\underset{R}{\overset{|}{H-C-}}}{\overset{R^2-Z-NH}{\underset{|}{\phantom{H-C-}}}}$$

where R is benzyl, phenyl, cyclopentyl, cyclohexyl, cyclopentyl-$CH_2$— or cyclohexyl-$CH_2$—;

Z is

—S(O)$_n$— or a bond;

R$^2$ is C$_1$–C$_6$ alkyl, C$_1$–C$_2$ perfluoroalkyl, —(CH$_2$)$_g$—COOH, C$_1$–C$_6$ alkoxy, (C$_1$–C$_4$ alkoxy)C$_1$–C$_4$ alkyl, cyclopentyl, cyclohexyl, (C$_5$–C$_6$ cycloalkyl)CH$_2$—, amino, mono (C$_1$C$_4$)alkylamino, di(C$_1$–C$_4$)alkylamino, unsubstituted or substituted aryl, where aryl is phenyl or naphthyl, unsubstituted or substituted benzyl, a 9 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

g is 1, 2 or 3;

n is 1 or 2; and pharmaceutically acceptable salts and solvates thereof;

provided that when R is benzyl, phenyl, cyclopentyl or cyclohexyl and Z is

or a bond, R$^2$ is other than C$_1$–C$_6$ alkyl, C$_1$–C$_2$ perfluoroalkyl, C$_1$–C$_6$ alkoxy or unsubstituted phenyl; and further provided that when Z is —S(O)n—, then R$^2$ is other than unsubstituted or substituted naphthyl or a 9 or 10 membered unsubstituted or substituted fused bicyclic heterocyclic ring.

74. The method of claim 73 where

R$^1$ is hydrogen;

X is prolinyl or azetidinyl-2-carbonyl;

Y is a group

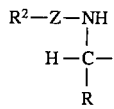

where R is benzyl, phenyl, cyclopentyl, cyclohexyl, cyclopentyl-CH$_2$— or cyclohexyl-CH$_2$—;

Z is

—S(O)n— or a bond;

R$^2$ is C$_1$–C$_6$ alkyl, C$_1$–C$_2$ perfluoroalkyl, C$_1$–C$_6$ alkoxy, (C$_1$–C$_4$ alkoxy)C$_1$–C$_4$ alkyl, cyclopentyl, cyclohexyl, (C$_5$–C$_6$ cycloalkyl)CH$_2$—, amino, mono (C$_1$–C$_4$)alkylamino, di(C$_1$C$_4$)alkylamino, unsubstituted or substituted aryl, where aryl is phenyl or naphthyl, unsubstituted or substituted benzyl, a 5 or 6 member unsubstituted or substituted heterocyclic ring, having one or two heteroatoms, one of which is nitrogen and the second heteroatom is selected from sulfur, oxygen and nitrogen, or methylene substituted with a 5 or 6 membered unsubstituted or substituted heterocyclic ring having one nitrogen atom or two hetero atoms one of which is nitrogen and the second heteroatom is selected from sulfur, oxygen and nitrogen; or a 9 or 10 membered unsubstituted or substituted fused bicyclic heterocyclic ring;

n is 1 or 2; and pharmaceutically acceptable salts and solvates thereof;

provided that when R is benzyl, phenyl, cyclopentyl or cyclohexyl and Z is

or a bond, R$^2$ is other than C$_1$–C$_6$alkyl, C$_1$–C$_2$ perfluoroalkyl, C$_1$–C$_6$ alkoxy or unsubstituted phenyl; and further provided that when Z is —S(O)n—, then R$^2$ is other than unsubstituted or substituted naphthyl or a 9 or 10 membered unsubstituted or substituted fused bicyclic heterocyclic ring.

75. The method of claim 74 where

R$^1$ is hydrogen;

R$^2$ is C$_1$–C$_6$ alkyl, amino, mono(C$_1$–C$_4$ alkyl)amino, di(C$_1$–C$_4$ alkyl)amino, or a 9 or 10 membered unsubstituted or monosubstituted fused bicyclic heterocyclic ring; and pharmaceutically acceptable salts and solvates thereof; provided that when R is benzyl, phenyl, cyclopentyl or cyclohexyl and Z is

or a bond, R$^2$ is other than C$_1$–C$_6$ alkyl, and further provided that when Z is —S(O)n—, then R$^2$ is other than unsubstituted or substituted naphthyl or a 9 or 10 membered unsubstituted or substituted fused bicyclic heterocyclic ring.

76. The method of claim 75 where

R$^1$ is hydrogen;

R is benzyl or cyclohexyl-CH$_2$—;

Z is

R$^2$ is a 9 10 membered unsubstituted or monosubstituted fused bicyclic heterocyclic ring containing one nitrogen atom and where the substituent is selected from C$_1$–C$_4$ alkyl, amino, mono(C$_1$–C$_4$ alkyl)amino, di(C$_1$–C$_4$alkyl)amino, and —NHSO$_2$(C$_1$–C$_4$ alkyl);

and pharmaceutically acceptable salts and solvates thereof.

77. The method of claim 75 where

R$^1$ is hydrogen;

Z is —SO$_2$—;

R$^2$ is C$_1$–C$_6$ alkyl, amino, mono(C$_1$–C$_4$ alkyl)amino or di(C$_1$–C$_4$ alkyl)amino;

and pharmaceutically acceptable salts and solvates thereof.

78. The method of claim 73 where

R$^1$ is hydrogen;

X is prolinyl or azetidinyl-2-carbonyl;

Z is a bond;

R is —(CH$_2$)$_g$—COOH;

g is 1, 2 or 3; and pharmaceutically acceptable salts and solvates thereof.

79. The method of claim 76 where said compound is N-(1-methylindolyl-2-carbonyl)-D-phenylalanyl-L-prolinyl-L-arginine aldehyde and pharmaceutically acceptable salts and solvates thereof.

80. The method of claim 76 where said compound is N-(quinolinyl-2-carbonyl)-D-phenylalanyl-L-prolinyl-L-arginine aldehyde and pharmaceutically acceptable salts and solvates thereof.

81. The method of claim 76 where said compound is N-(1-methylindolyl-2-carbonyl)-D-cyclohexylalanyl-L-prolinyl-L-arginine aldehyde and pharmaceutically acceptable salts and solvates thereof.

82. The method of claim 76 where said compound is N-(quinolinyl-2-carbonyl-D-cyclohexylalanyl-L-prolinyl-L-arginine aldehyde and pharmaceutically acceptable salts and solvates thereof.

83. The method of claim 77 where said compound is N-(methylsulfonyl)-D-phenylalanyl-L-prolinyl-L-arginine aldehyde and pharmaceutically acceptable salts and solvates thereof.

84. The method of claim 77 where said compound is N-(ethylsulfonyl)-D-phenylalanyl-L-prolinyl-L-arginine aldehyde and pharmaceutically acceptable salts and solvates thereof.

85. The method of claim 77 where said compound is N-(n-Propylsulfonyl)-D-phenylalanyl-L-prolinyl-L-arginine aldehyde and pharmaceutically acceptable salts and solvates thereof.

86. The method of claim 77 where said compound is N-(dimethylaminosulfonyl)-D-phenylalanyl-L-prolinyl-L-arginine aldehyde and pharmaceutically acceptable salts and solvates thereof.

87. The method of claim 77 where said compound is N-(ethylsulfonyl)-D-phenylglycinyl-L-prolinyl-L-arginine aldehyde and pharmaceutically acceptable salts and solvates thereof.

88. The method of claim 77 where said compound is N-(ethylsulfonyl)-D-cyclohexylalanyl-L-prolinyl-L-arginine aldehyde and pharmaceutically acceptable salts and solvates thereof.

89. The method of claim 77 where said compound is N-(ethylsulfonyl)-D-cyclohexylglycinyl-L-prolinyl-L-arginine aldehyde and pharmaceutically acceptable salts and solvates thereof.

90. The method of claim 78 where said compound is N-(carboxymethyl)-D-cyclohexylalanyl-L-prolinyl-L-arginine aldehyde and pharmaceutically acceptable salts and solvates thereof.

* * * * *

UNITED STATES PATENT AND TRADEMARK OFFICE
CERTIFICATE OF CORRECTION

PATENT NO. : 5,602,101
DATED : February 11, 1997
INVENTOR(S) : Aaron L. Schacht, et al It is certified that error appears in the above-indentified patent and that said Letters Patent is hereby corrected as shown below:

On the title page:

Item [56]
, listed under "FOREIGN PATENT DOCUMENTS" at the next to last listing, WO95/09858, the date "4/1994" should be deleted and the date "4 substituted therefor. Item [56]
, listed under "OTHER PUBLICATIONS" at the entry begins "Claeson, et al.," the date "June 16-14 21, 1991," should be deleted and date "June 16-21, 1991," should be substituted therefor.

In column 1, line 47, the number "96" should be deleted and the number "36" substituted therefor.

In column 2, line 61 the listing "$C_1-C_2$" should be deleted and "$C_1-C_2$" should be substituted therefor.

In column 6, lines 56 through 64, the existing structure should be deleted and following structure substituted therefor:

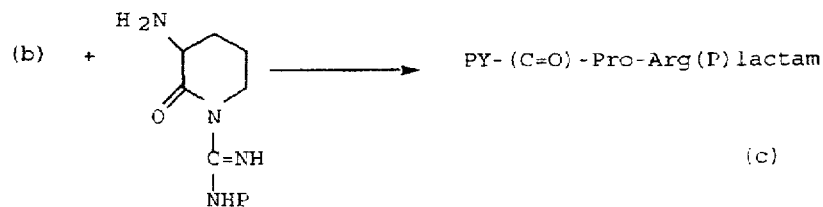

UNITED STATES PATENT AND TRADEMARK OFFICE
CERTIFICATE OF CORRECTION

PATENT NO.  : 5,602,101
DATED       : February 11, 1997
INVENTOR(S) : Aaron L. Schacht, et al It is certified that error appears in the above-indentified patent and that said Letters Patent is hereby corrected as shown below:

Column 54, line 23, following "the" the word "formula" should be added.

Column 57, Claim 13, line 1, Claim 14-line 4, Claim 17, line 13, and Claim 18, line 16, following the word "which" the letters "ms" appear Those entries of "ms" should be deleted and "is" substituted therefor.

In column 62, line 20, claim 40, the number "34" appears. This number should be deleted and the number "39" should be substituted therefor.

In column 68, line 50, the number "9 10" should be deleted and "9 or 10" should be substitued therefor.

Signed and Sealed this

Ninth Day of November, 1999

*Attest:*

Q. TODD DICKINSON

*Attesting Officer*    Acting Commissioner of Patents and Trademarks